United States Patent
Mates et al.

(10) Patent No.: US 10,117,867 B2
(45) Date of Patent: *Nov. 6, 2018

(54) METHODS AND COMPOSITIONS FOR SLEEP DISORDERS AND OTHER DISORDERS

(71) Applicant: INTRA-CELLULAR THERAPIES, INC., New York, NY (US)

(72) Inventors: Sharon Mates, New York, NY (US); Allen Fienberg, New York, NY (US); Lawrence P. Wennogle, Hillsborough, NJ (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/467,867

(22) Filed: Mar. 23, 2017

(65) Prior Publication Data

US 2017/0189398 A1 Jul. 6, 2017

Related U.S. Application Data

(60) Continuation of application No. 14/885,813, filed on Oct. 16, 2015, now Pat. No. 9,616,061, which is a continuation of application No. 14/066,987, filed on Oct. 30, 2013, now Pat. No. 9,168,258, which is a division of application No. 12/994,560, filed as application No. PCT/US2009/003261 on May 27, 2009, now Pat. No. 8,598,119.

(60) Provisional application No. 61/155,032, filed on Feb. 24, 2009, provisional application No. 61/056,433, filed on May 27, 2008.

(51) Int. Cl.

| | |
|---|---|
| *A61K 31/44* | (2006.01) |
| *A61K 31/4985* | (2006.01) |
| *A61K 31/5383* | (2006.01) |
| *A61K 45/06* | (2006.01) |
| *C07D 471/14* | (2006.01) |
| *C07D 498/14* | (2006.01) |
| *A61K 9/00* | (2006.01) |
| *A61K 31/198* | (2006.01) |

(52) U.S. Cl.
CPC ........ *A61K 31/4985* (2013.01); *A61K 9/0053* (2013.01); *A61K 31/198* (2013.01); *A61K 31/44* (2013.01); *A61K 31/5383* (2013.01); *A61K 45/06* (2013.01); *C07D 471/14* (2013.01); *C07D 498/14* (2013.01)

(58) Field of Classification Search
CPC .. A61K 31/198; A61K 31/44; A61K 31/4985; A61K 31/5383; A61K 45/06; A61K 9/0053; C07D 471/14; C07D 498/14
See application file for complete search history.

(56) References Cited

U.S. PATENT DOCUMENTS

| | | |
|---|---|---|
| 5,114,976 A | 5/1992 | Norden |
| 5,151,419 A | 9/1992 | Perenyi et al. |
| 6,548,493 B1 | 4/2003 | Robichaud et al. |
| 6,552,017 B1 | 4/2003 | Robichaud et al. |
| 6,713,471 B1 | 3/2004 | Robichaud et al. |
| 7,071,186 B2 | 7/2006 | Robichaud et al. |
| 7,081,455 B2 | 7/2006 | Robichaud et al. |
| 7,183,282 B2 | 2/2007 | Robichaud et al. |
| RE39,679 E | 6/2007 | Robichaud et al. |
| RE39,680 E | 6/2007 | Robichaud et al. |
| 7,238,690 B2 | 7/2007 | Robichaud et al. |
| 7,645,752 B2 | 1/2010 | McDevitt et al. |
| 7,998,971 B2 * | 8/2011 | Barlow ............. A61K 31/4355 514/292 |
| 8,598,119 B2 | 12/2013 | Mates et al. |
| 8,648,077 B2 | 2/2014 | Tomesch et al. |
| 8,779,139 B2 | 7/2014 | Tomesch et al. |
| 8,993,572 B2 | 3/2015 | Mates et al. |
| 9,168,258 B2 | 10/2015 | Mates et al. |
| 9,199,995 B2 | 12/2015 | Tomesch et al. |
| 9,616,061 B2 | 4/2017 | Mates et al. |
| 2004/0220178 A1 | 11/2004 | Robichaud et al. |
| 2005/0222209 A1 | 10/2005 | Zeldis et al. |
| 2006/0205787 A1 | 9/2006 | Muller et al. |
| 2007/0203120 A1 | 8/2007 | McDevitt et al. |
| 2014/0364609 A1 | 12/2014 | Tomesch et al. |
| 2015/0072964 A1 | 3/2015 | Mates et al. |
| 2015/0079172 A1 | 3/2015 | Mates et al. |
| 2015/0080404 A1 | 3/2015 | Mates et al. |
| 2015/0166540 A1 | 6/2015 | Mates et al. |
| 2016/0031885 A1 | 2/2016 | Li et al. |
| 2016/0310502 A1 * | 10/2016 | Vanover ............. A61K 31/4985 |

FOREIGN PATENT DOCUMENTS

| | | |
|---|---|---|
| WO | WO 2000/077002 | 12/2000 |
| WO | WO 2006/081251 | 8/2006 |

(Continued)

OTHER PUBLICATIONS

Marek et al. Synergistic Action of 5-HT2A Antagonists and Selective Serotonin Reuptake Inhibitors in Neuropsychiatric Disorders. Neuropsychopharmacology, 2003. vol. 28, pp. 402-412. (Year: 2003).*

(Continued)

*Primary Examiner* — Marcela M Cordero Garcia
(74) *Attorney, Agent, or Firm* — Hoxie & Associates LLC

(57) ABSTRACT

Use of particular substituted heterocycle fused gamma-carboline compounds as pharmaceuticals and pharmaceutical compositions comprising them for the treatment of one or more disorders involving the 5-HT2A, SERT and/or dopamine D2 pathways are disclosed. In addition, the compounds may be combined with other therapeutic agents for the treatment of one or more sleep disorders, depression, psychosis, dyskinesias, and/or Parkinson's disease or any combinations.

28 Claims, No Drawings

FOREIGN PATENT DOCUMENTS

| WO | WO 2007/025103 | 3/2007 |
| WO | WO 2007/084841 | 7/2007 |
| WO | WO 2008/112280 | 9/2008 |
| WO | WO 2009/017836 | 2/2009 |
| WO | WO 2009/145900 | 12/2009 |

OTHER PUBLICATIONS

Angst et al. Prevalence and Characteristics of Undiagnosed Bipolar Disorders in Patients With a Major Depressive Episode. Arch Gen Psychiatry, 2011. vol. 68, No. 8, pp. 701-709. (Year: 2011).*

Alvir et al. Clozapine-Induced Agranulocytosis. The New England Journal of Medicine, vol. 329, No. 3, pp. 162-167, (1993). International Search Report of the International Searching Authority (US) dated Jul. 16, 2009 for corresponding International Application No. PCT/US2009/003261.

ITI-007 in the treatment of schizophrenia: from novel pharmacology to clinical outcomes. Expert Review of Neurotherapeutics, vol. 16, No. 6, pp. 601-614, (2016).

Fitzgerald, et al. "Inhibition of Caries in hamsters by 2-Deoxy-D-glucose", J. Dent 56:1431-1431 (1977).

Rye (Sleep Disorders and Parkinson's Disease, 2000, accessed online http://www.waparkinsons.org/edu_research/articles/Sleep_Disorders.html), 2 pages.

Davis et al. "ITI-007 demonstrates brain occupancy at serotonin 5-HT2A and dopamine D2 receptors and serotonin transporters using positron emission tomography in healthy volunteers", Psychopharmacology, Published Online Apr. 7, 2015, pp. 1-10.

Perlis et al., "Clinical Features of Bipolar Depression Versus Major Depressive Disorder in Large Multicenter Trials", Am J Psychiatry, vol. 163, p. 225-231, (2006).

* cited by examiner

METHODS AND COMPOSITIONS FOR SLEEP DISORDERS AND OTHER DISORDERS

CROSS REFERENCE TO RELATED APPLICATIONS

This application is a continuation of U.S. application Ser. No. 14/885,813, filed on Oct. 16, 2015, which is a continuation application of U.S. application Ser. No. 14/066,987, filed on Oct. 30, 2013, which is a divisional of U.S. application Ser. No. 12/994,560, filed on Nov. 24, 2010, which is a United States National Stage Application under 35 U.S.C. § 371 of PCT/US2009/003261 filed on May 27, 2009, which claims benefit of U.S. Provisional Application No. 61/056,433, filed on May 27, 2008, and U.S. Provisional Application No. 61/155,032, filed on Feb. 24, 2009, the contents of each of which are incorporated herein by reference.

This application claims the benefit of U.S. Provisional Application Nos. 61/056,433 filed on May 27, 2008 and 61/155,032 filed on Feb. 24, 2009, both of which applications are hereby incorporated by reference.

TECHNICAL FIELD

The present invention relates to use of particular substituted heterocycle fused gamma-carbolines as described herein, in free or pharmaceutically acceptable salt forms, as pharmaceuticals and pharmaceutical compositions, e.g., in the treatment of diseases involving 5-HT2A receptor, serotonin transporter (SERT) and/or dopamine $D_2$ receptor protein phosphorylation pathways, such as depression, sleep disorders, and mood disorders associated with psychosis or Parkinson's disease; psychosis such as schizophrenia associated with depression; bipolar disorder; and other psychiatric and neurological conditions such as sleep disorders, as well as to combinations with other agents.

BACKGROUND OF THE INVENTION

Psychosis such as schizophrenia is a severe and crippling mental disorder that affects about 1% of the population. It is a mental disorder that is characterized by gross impairment in reality, major disturbances in reasoning, often evidenced by delusions and hallucinations, incoherent speech, and/or disorganized and agitated behavior. Several classes of antipsychotic drugs are available for treatment of schizophrenia, including the prototypical antipsychotic drugs such as chlorpromazine and haloperidol as well as many others such as droperidol, fluphenazine, loxapine, mesoridazine molidone, perphenazine, pimozide, prochlorperazine promazine, thioridazine, thiothixene, and trifluoperazine. While these agents are effective in treating positive symptoms of psychosis such as symptoms of hallucination and delusions, e.g., in schizophrenia, these drugs often cause both short-term and long-term movement disorders and other side effects including acute dystonia (e.g., facial grimacing, torticollis, oculogyric crisis, abnormal contraction of spinal muscles and of muscles involved in breathing), akathisia, bradykinesia, rigidity or short term paralysis, parkinsonism, sedation, dry mouth, sexual dysfunction and sometimes tardive dyskinesia. Tardive dyskinesia may persist after discontinuation of the use of typical antipsychotic agents and there is no effective treatment of such side effects. Because of the severity of the side effects, typical antipsychotic drugs, though effective in treating the mental and emotional aspect of the disorder, do not help patients to function normally in society.

Although another class of antipsychotic agents called atypical antipsychotic agents, which include clozapine, aripiparazole, olanzapine, quetiapine, risperidone and ziprasidone (atypical antipsychotic agents) are effective in treating positive and negative symptoms of schizophrenia with fewer extrapyramidal side effects, these agents can nevertheless cause other serious and at times fatal side effects, including bone marrow suppression, seizure, orthostatic hypotension, insomnia, sedation, somnolence, weight gain, and if administered at higher doses, may again cause extrapyramidal side effects. Therefore, atypical antipsychotic agents, though have improved clinical profiles, are nevertheless undesirable.

In addition to the positive and negative symptoms of psychosis (e.g., schizophrenia), many psychotic patients often times also suffer from depression. While both typical and atypical antipsychotic agents are effective in treating psychosis, depression is often times neglected or left undertreated. The combination of psychosis and depression poses a particular challenge in their treatment as studies revealed that up to 10% of the patients suffering from schizophrenia end their own lives. Therefore, there is a need for agents that are useful for the treatment of psychosis in depressed patients, and for the treatment of depression as well as other disorders such as sleep and mood disorders in psychotic patients and patients suffering from Parkinson's disease without exhibiting or exhibiting minimal extrapyramidal and other side effects compared to conventional antipsychotic, hypnotic and anti-depressive agents.

Substituted heterocycle fused gamma-carbolines are known to be agonists or antagonists of 5-HT2 receptors, particularly 5-HT2A and 5-HT2C receptors, in treating central nervous system disorders. These compounds have been disclosed in U.S. Pat. Nos. 6,548,493; 7,238,690; 6,552,017; 6,713,471; U.S. RE39680, and U.S. RE39679, as novel compounds useful for the treatment of disorders associated with 5-HT2A receptor modulation such as obesity, anxiety, depression, psychosis, schizophrenia, sleep disorders, sexual disorders migraine, conditions associated with cephalic pain, social phobias, and gastrointestinal disorders such as dysfunction of the gastrointestinal tract motility. PCT/US08/03340 and U.S. application Ser. No. 10/786,935 also disclose methods of making substituted heterocycle fused gamma-carbolines and uses of these gamma-carbolines as serotonin agonists and antagonists useful for the control and prevention of central nervous system disorders such as addictive behavior and sleep disorders. Although these references disclose use of substituted heterocycle fused gamma-carbolines to independently treat disorders associated with serotonin pathways such as sleep disorder, depression, psychosis, and schizophrenia associated with the $5\text{-HT}_{2A}$ pathways, there is no teaching that specific compounds of substituted heterocycle fused gamma-carbolines also exhibit nanomolar binding affinity to serotonin reuptake transporter (SERT) and dopamine $D_2$ receptors and therefore may be used to treat a combination of psychosis and depressive disorders as well as sleep, depressive and/or mood disorders in patients with psychosis or Parkinson's disease.

In addition to disorders associated with psychosis and/or depression, these references do not disclose use of particular substituted heterocycle fused gamma-carbolines at a low dose to selectively antagonize $5\text{-HT}_{2A}$ receptors without affecting or minimally affecting dopamine $D_2$ receptors, thereby useful for the treatment of sleep disorders without the side effects of the dopamine $D_2$ pathways or side effects of other pathways (e.g., $GABA_A$ receptors) associated with convention sedative-hypnotic agents (e.g., benzodiazepines) including but not limited to the development of drug dependency, muscle hypotonia, weakness, headache, blurred vision, vertigo, nausea, vomiting, epigastric distress, diarrhea, joint pains, and chest pains.

SUMMARY OF THE INVENTION

It has been discovered that particular substituted heterocycle fused gamma-carboline compounds (Compounds of Formula I, described hereinbelow) exhibit unique pharmacological characteristics wherein they possess high affinity for serotonin 5-HT2A receptors and moderate, yet nanomolar affinity for dopamine receptors and serotonin reuptake transporter (SERT). The compounds moreover demonstrate selectivity between dopamine D1 and D2 receptors. This is a new and unexpected binding profile, which gives the compounds particular utility in certain indications as described below, and in combination therapies.

At low doses, Compounds of Formula I selectively antagonize 5-HT2A receptors and increases rapid eye movement (REM) and non-REM sleep in animals. Therefore, at low doses, these compounds may be used to improve sleep maintenance insomnia and insomnia associated with neuropsychiatric and neurologic disorders.

In a clinical trial, low doses (e.g., 1, 5, and 10 mg) of Compounds of Formula I, e.g. Compound A, dose-dependently increase slow wave sleep, consistent with $5\text{-}HT_{2A}$ receptor antagonism, they dose-dependently decreases wake after sleep onset, consistent with improving sleep maintenance, they increase total sleep time and restore normal sleep architecture to patients with insomnia by increasing slow wave sleep early in the night and increasing stage 2 sleep late in the night, toward morning, they show no early-morning rebound insomnia and did not suppress REM sleep. They do not impair next-day cognitive function. The magnitude of WASO decrease and total sleep time increase at 10 mg suggests the modest D2 (and possibly SERT and D1) occupancy at this dose contributes favorably to the sleep profile beyond simple 5-HT2A receptor antagonism. Dopamine receptor modulation and SERT inhibition improve psychiatric symptoms co-morbid with insomnia. Compounds of Formula I represent a new approach for treating sleep maintenance insomnia and sleep disorders associated with neuropsychiatric and neurological diseases, as well as for the treatment of sleep disorders, schizophrenia, and other neuropsychiatric and neurological indications.

At higher doses, when 5-HT2A receptors are fully occupied, Compounds of Formula I modulate dopamine receptor protein phosphorylation. Therefore, Compounds of Formula I are particularly useful for the treatment of sleep disorders in patients suffering from psychosis such as schizophrenia, Parkinson's disease and/or depression.

Unlike dopamine receptor antagonists, Compounds of Formula I normalize brain dopamine activity, particularly in the prefrontal cortex. In addition, Compounds of Formula I also moderately bind to SERT. Therefore, Compounds of Formula I are particularly useful for the treatment of psychosis in patients suffering from depression. Unlike many traditional antipsychotic drugs, Compounds of Formula I show an improved selectivity profile with respect to off-target interactions such as adrenergic alpha-1a, serotonin 5-HT2C, and histamine H1 associated with many side effects compared to other antipsychotic drugs. Compounds of Formula I are therefore also useful as antipsychotic agents in patients who are unable to tolerate the side effects of convention antipsychotic drugs.

In addition to binding to 5-HT2A and dopamine $D_2$ receptors, Compounds of Formula I also exhibit nanomolar binding affinity for SERT compared to known antidepressants. Therefore, Compounds of Formula I are useful for the treatment of depression in patients suffering from psychosis.

Because Compounds of Formula I have a wider separation between $5\text{-}HT_{2A}$ and $D_2$ receptor affinities than other atypical antipsychotic drugs (~60 fold), they are additionally useful in reduction of dyskinesia. For example, they reduce L-DOPA-induced dyskinetic behavior in a mouse model. Without intending to be bound by theory, it is hypothesized that this is accomplished by virtue of the potent $5\text{-}HT_{2A}$ antagonism with minimal interference with L-DOPA-induced motor correction, by virtue of the low relative $D_2$ receptor activity. Parkinson's disease results from loss of DA neurons in the substantia nigra pars compacta. The primary motor symptoms of PD are treated by L-DOPA. Activation of medium spiny neurons in the dorsolateral striatum that project to the substantia nigra pars reticulata results in disinhibition of thalamocortical neurons and increased motor activity. Overactivity of this "direct" striatal pathway may contribute to the expression of dyskinesias, such as are commonly seen in PD patients being treated with dopaminergic drugs such as L-dopa. $5\text{-}HT_{2A}$ receptors are localized in striatal medium spiny neurons. Compounds of Formula I are thus believed to block dyskinesias by blockade of $5\text{-}HT_{2A}$ receptors.

Therefore, the invention provides methods as follows:

A method (Method I) for the treatment of one or more disorders involving serotonine $5\text{-}HT_{2A}$, dopamine D2 and/or serotonin reuptake transporter (SERT) pathway, comprising administering to a patient in need thereof a Compound of Formula I:

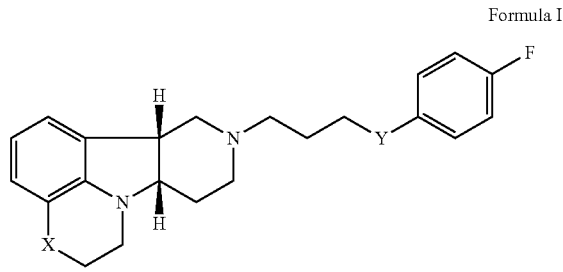

Formula I wherein X is O, —NH or —N(CH$_3$); and Y is —O— or —C(O)—, in free or pharmaceutically acceptable salt form, at a dose which selectively blocks $5\text{-}HT_{2A}$ receptors.

The invention further provides Method I as follows:
1.1 Method I comprising a compound of Formula I, wherein X is —N(CH$_3$);
1.2 Method I comprising a compound of Formula I, wherein X is —NH;
1.3 Method I comprising a compound of Formula I, wherein X is O;
1.4 Method I or any of 1.1-1.3, comprising a compound of Formula I, wherein Y is —C(O)—;
1.5 Method I or any of 1.1-1.3, comprising a compound of Formula I, wherein Y is —O—;
1.6 any of the preceding methods wherein the Compound of Formula I is selected from a group consisting of:

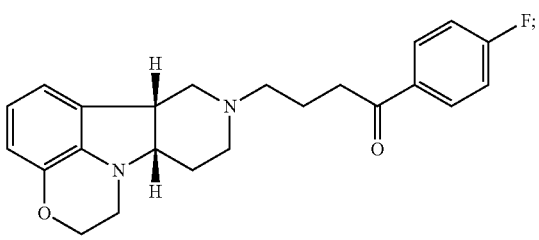
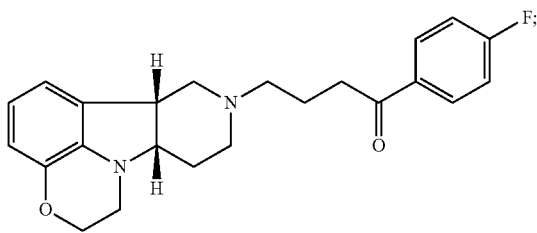 [SMILES: O=C(CCCN1CC[C@H]2[C@@H](C1)c1cccc3c1N2CCO3)c1ccc(F)cc1]
1.8 any of the preceding methods wherein the Compound of Formula I is:
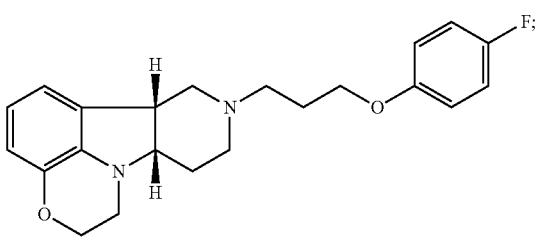
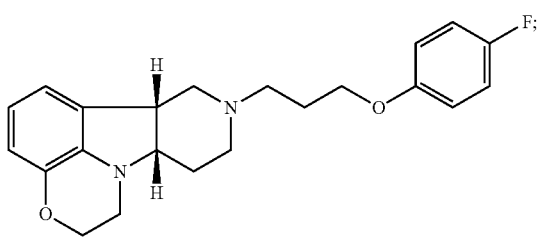 [SMILES: Fc1ccc(OCCCN2CC[C@H]3[C@@H](C2)c2cccc4c2N3CCO4)cc1]
1.9 any of the preceding methods wherein the Compound of Formula I is:
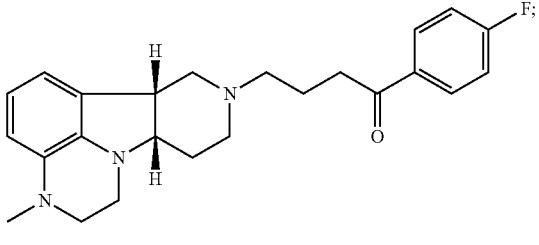
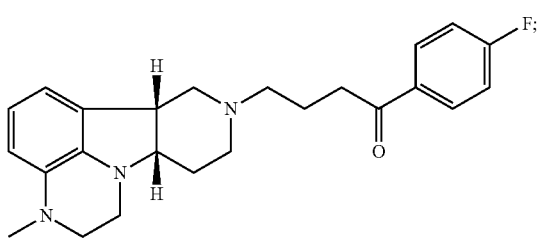 [SMILES: CN1CCN2c3c(cccc31)[C@@H]1CN(CCCC(=O)c3ccc(F)cc3)CC[C@@H]12]
1.10 any of the preceding methods wherein the Compound of Formula I is:
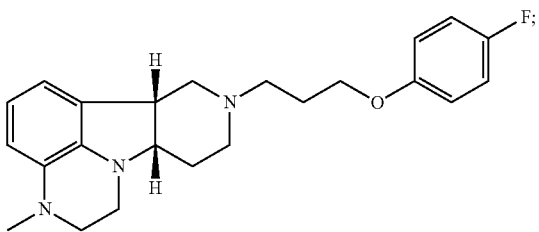 [SMILES: CN1CCN2c3c(cccc31)[C@@H]1CN(CCCOc3ccc(F)cc3)CC[C@@H]12]
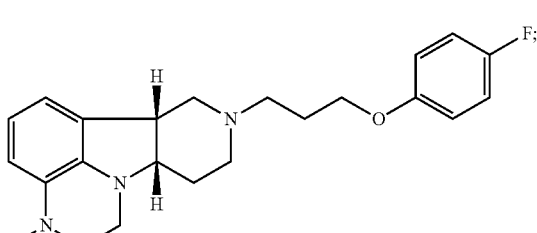
1.11 any of the preceding methods wherein the Compound of Formula I is:
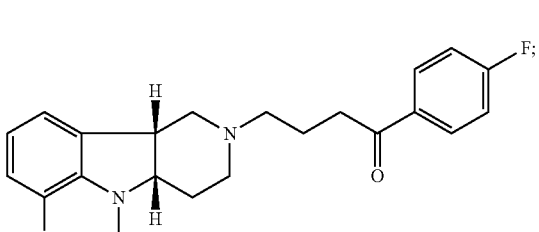
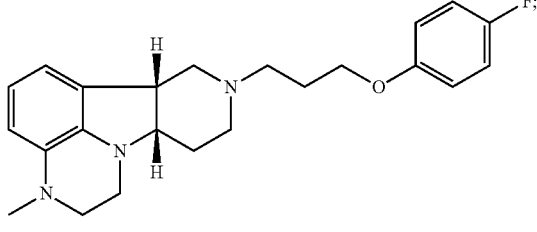
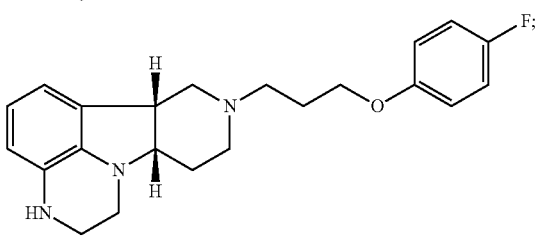
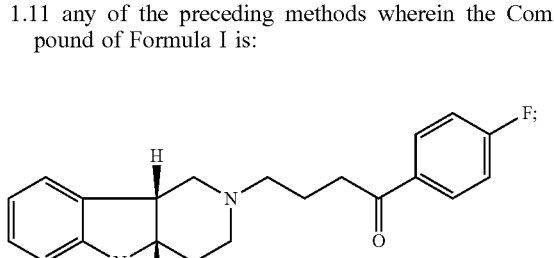
1.7 any of the preceding methods wherein the Compound of Formula I is:

1.12 any of the preceding methods wherein the Compound of Formula I is:

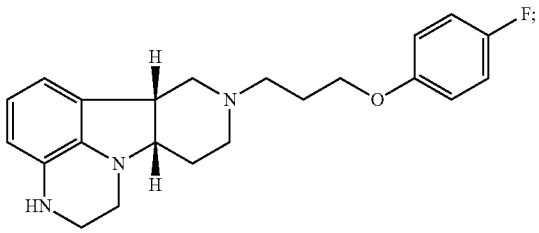 [SMILES: Fc1ccc(OCCCN2CC[C@H]3[C@@H](C2)c2cccc4c2N3CCN4)cc1]

1.13 any of the preceding methods wherein the Compounds of Formula I (i) bind to 5-HT2A receptors, e.g., with a $K_i$ of less than 50 nM, more preferably less 10 nM, still more preferably less than 5 nM, most preferably less than 1 nM; and (ii) also bind to dopamine $D_2$ receptors and SERT, e.g., with a $K_i$ of less than 100 nM, preferably less than 75 nM, more preferably less 50 nM, in a binding assay as described in Example 1 below;

1.14 any of the preceding methods wherein the Compounds of Formula I (i) bind to 5-HT2A, e.g., with a $K_i$ of less than 5 nM, preferably less than 1 nM, and (ii) also bind to dopamine $D_2$ receptors and SERT, e.g., with a $K_i$ of less than 100 nM, preferably less than 75 nM, more preferably less than 50 nM in a binding assay as described in Example 1 below;

1.15 any of the preceding methods wherein the Compounds of Formula I (i) bind to 5-HT2A, e.g., with a $K_i$ of less than 1 nM and (ii) bind to dopaimine $D_2$ receptors, e.g., with a $K_i$ of about 25-75 nM; and (iii) also bind to SERT, e.g., with a $K_i$ of less than 100 nM, preferably less than 75 nM, more preferably less 50 nM, in a binding assay as described in Example 1 below;

1.16 any of the preceding methods wherein the Compounds of Formula I does not bind to adrenergic alpha-1a receptors (α1A) or bind to α1A receptors, e.g., with a $K_i$ of greater than 75 nM, preferably greater than 100 nM in a binding assay as described in Example 1 below;

1.17 any of the preceding methods wherein the Compounds of Formula I does not bind to 5-HT2C receptors, or bind to 5-HT2C receptors e.g., with a $K_i$ of greater than 75 nM, preferably greater than 100 nM, more preferably greater than 150 nM in a binding assay as described in Example 1 below;

1.18 any of the preceding methods wherein the Compounds of Formula I does not bind to H1 receptors, or bind to H1 receptors, e.g., with a $K_i$ of greater than 500 nM, preferably greater than 750 nM, more preferably greater than 1000 nM in a binding assay as described in Example 1 below;

1.19 any of the preceding methods wherein the Compounds of Formula I (i) bind to $5\text{-HT}_{2A}$, e.g., with a $K_i$ of less than 5 nM, preferably less than 1 nM, (ii) bind to dopamine $D_2$ receptors, e.g., with a $K_i$ of 25-75 nM; (iii) bind to SERT, e.g., with a $K_i$ of less than 100 nM, preferably less than 75 nM, more preferably less 50 nM; and (iv) does not bind to α1A, 5-HT2C and/or H1 receptors, or bind to α1A, 5-HT2C and/or H1 receptors e.g., with a $K_i$ of greater than 75 nM in a binding assay as described in Example 1 below;

1.20 any of the preceding methods wherein said one or more disorders are selected from (1) psychosis, e.g., schizophrenia, in a patient suffering from depression; (2) depression in a patient suffering from psychosis, e.g., schizophrenia; (3) mood disorders associated with psychosis, e.g., schizophrenia, or Parkinson's disease; and (4) sleep disorders associated with psychosis, e.g., schizophrenia, or Parkinson's disease;

1.21 Method I or any of 1.1-1.20, wherein said disorder is psychosis, e.g., schizophrenia and said patient is a patient suffering from depression;

1.22 Method I or any of 1.1-1.21, wherein said patient is unable to tolerate the side effects of convention antipsychotic drugs, e.g., chlorpromazine, haloperidol droperidol, fluphenazine, loxapine, mesoridazine molidone, perphenazine, pimozide, prochlorperazine promazine, thioridazine, thiothixene, trifluoperazine, clozapine, aripiparazole, olanzapine, quetiapine, risperidone and ziprasidone;

1.23 Method I or any of 1.1-1.21, wherein said patient is unable to tolerate the side effects of convention antipsychotic drugs, e.g., haloperidol, aripiparazole, clozapine, olanzapine, quetiapine, risperidone, and zipasidone;

1.24 Method I or any of 1.1-1.20, wherein said disorder is depression and said patient is a patient suffering from psychosis, e.g., schizophrenia, or Parkinson's disease;

1.25 Method I or any of 1.1-1.20, wherein said one or more disorders is sleep disorder and said patient is suffering from depression;

1.26 Method I or any of 1.1-1.20, wherein said one or more disorders is sleep disorder and said patient is suffering from psychosis, e.g., schizophrenia;

1.27 Method I or any of 1.1-1.20, wherein said one or more disorders is sleep disorder and said patient is suffering from Parkinson's disease;

1.28 Method I or any of 1.1-1.20 or 1.25-1.27, wherein said one or more disorders is sleep disorder and said patient is suffering from depression and psychosis, e.g., schizophrenia, or Parkinson's disease;

1.29 Any of the foregoing methods, wherein the effective amount is an amount sufficient to bind to SERT, 5-HT2A and $D_2$ receptors, e.g., with a $K_i$ of less than 100 nM, preferably less than 75 nM, more preferably less than 50 nM in an assay as described in Example 1 below;

1.30 Any of the foregoing methods, wherein the effective amount is an amount sufficient to (i) bind to SERT, 5-HT2A and $D_2$ receptors, e.g., with a $K_i$ of less than 100 nM, preferably less than 75 nM, more preferably less than 50 nM, and (ii) does not bind to α1A, 5-HT2C and/or H1 receptors or bind to α1A, 5-HT2C and/or H1 receptors, e.g., with a $K_i$ of greater than 50 nM, preferably greater than 75 nM in a binding assay as described in Example 1 below;

1.31 Any of the foregoing methods, wherein the effective amount is an amount sufficient to bind to 5-HT2A, e.g., with a $K_i$ of less than 5 nM, preferably less than 1 nM, and also bind to dopamine $D_2$ receptors and SERT, e.g., with a $K_i$ of less than 100 nM, preferably less than 75 nM, more preferably less than 50 nM in a binding assay as described in Examples 1 below;

1.32 Any of the foregoing methods, wherein the effective amount is an amount sufficient to (i) bind to 5-HT2A, e.g., with a $K_i$ of less than 5 nM, preferably less than 1 nM; (ii) bind to dopamine $D_2$ receptors, e.g., with a $K_i$ of 25-75 nM; (iii) bind to SERT, e.g., with a $K_i$ of less than 100 nM, preferably less than 75 nM, more preferably less than 50 nM; and (iv) does not bind to α1A, 5-HT2C and/or H1 receptors, or bind to α1A, 5-HT2C and/or H1 receptors, e.g., with a $K_i$ of greater than 50 nM, preferably greater than 75 nM in a binding assay as described in Examples 1 below;

1.33 Any of the foregoing methods, wherein the ratio of the $K_i$ of dopamine $D_2$ to the $K_i$ of 5-HT2A is greater than 25, preferably greater than 50;

1.34 Any of the foregoing methods, wherein ratio of the $K_i$ of α1A to the $K_i$ of 5-HT2A is greater than 25, preferably greater than 50, more preferably greater than 100, most preferably greater than 125;

1.35 Any of the foregoing methods, wherein ratio of the $K_i$ of 5HT2C to the $K_i$ of 5-HT2A is greater than 150, more preferably greater than 300;

1.36 Any of the foregoing methods, wherein ratio of the $K_i$ of H1 to the $K_i$ of 5-HT2A is greater than 100, more preferably greater than 200;

1.37 Any of the foregoing methods, wherein the effective amount is 1 mg-100 mg, preferably 2.5-50 mg.

1.38 Any of the foregoing methods wherein a condition to be treated is dyskinesia, e.g. in a patient receiving dopaminergic medications, e.g., medications selected from levodopa and levodopa adjuncts (carbidopa, COMT inhibitors, MAO-B inhibitors), dopamine agonists, and anticholinergics, e.g., levodopa.

1.39 Any of the foregoing methods wherein the patient suffers from Parkinson's disease.

A method (Method II) for the treatment of one or more sleep disorders comprising administering to a patient in need thereof a Compound of Formula I:

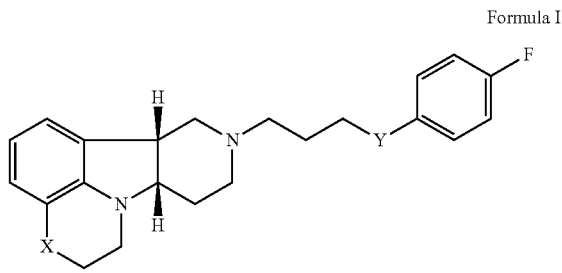

Formula I wherein X is O, —NH or —N(CH₃); and Y is —O— or —C(O)—, in free or pharmaceutically acceptable salt form, at a dose selective for 5-HT$_{2A}$ receptor blockade, e.g a daily dose of 0.1-20 mg, e.g., 0.5-10 mg.

The invention further provides Method II as follows:

2.1 Method II comprising a compound of Formula I, wherein X is —N(CH₃);

2.2 Method II comprising a compound of Formula I, wherein X is —NH;

2.3 Method II comprising a compound of Formula I, wherein X is O;

2.4 Method II or any of 2.1-2.3, comprising a compound of Formula I, wherein Y is —C(O)—;

2.5 Method II or any of 2.1-2.3, comprising a compound of Formula I, wherein Y is —O—;

2.6 any of the preceding methods wherein the Compound of Formula I is selected from a group consisting of:

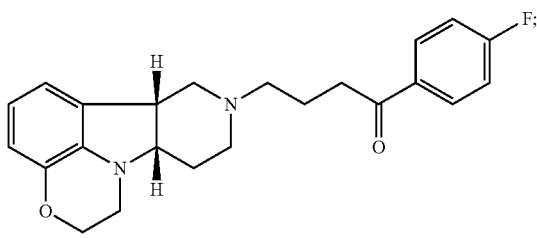 [SMILES: O=C(CCCN1CC[C@H]2[C@@H](C1)c1cccc3c1N2CCO3)c1ccc(F)cc1]

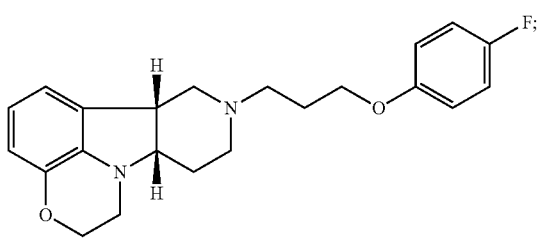 [SMILES: Fc1ccc(OCCCN2CC[C@H]3[C@@H](C2)c2cccc4c2N3CCO4)cc1]

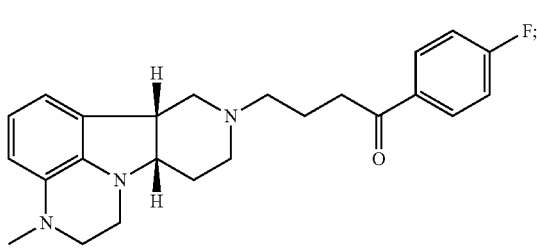

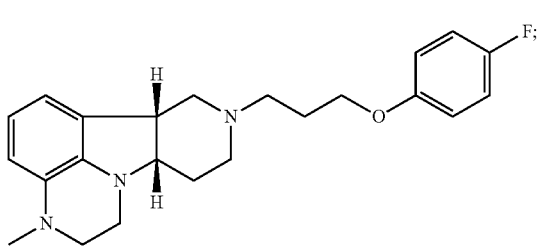

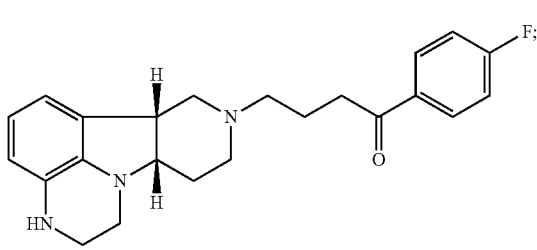

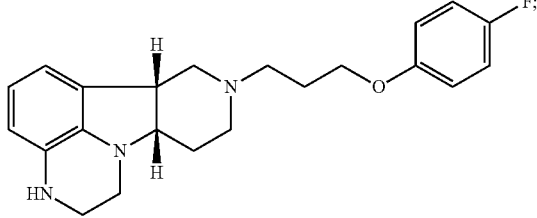

2.7 any of the preceding methods wherein the Compound of Formula I is:

2.8 any of the preceding methods wherein the Compound of Formula I is:

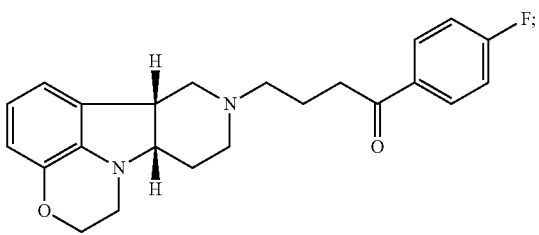

2.9 any of the preceding methods wherein the Compound of Formula I is:

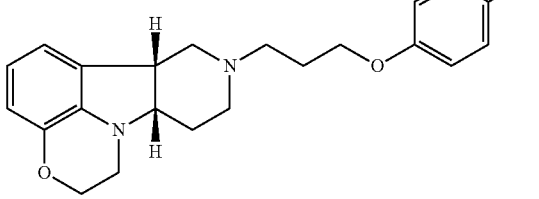

2.10 any of the preceding methods wherein the Compound of Formula I is:

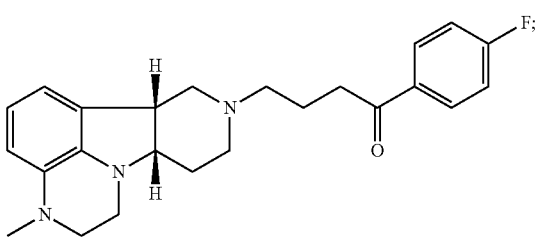 [SMILES: CN1CCN2c3c(cccc31)[C@@H]1CN(CCCC(=O)c3ccc(F)cc3)CC[C@@H]12]

2.11 any of the preceding methods wherein the Compound of Formula I is:

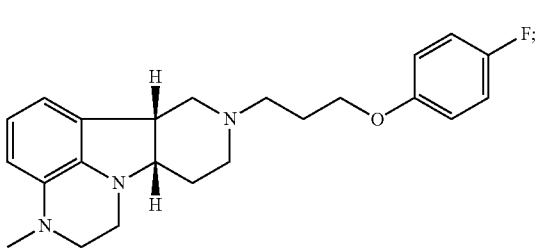 [SMILES: CN1CCN2c3c(cccc31)[C@@H]1CN(CCCOc3ccc(F)cc3)CC[C@@H]12]

2.12 any of the preceding methods wherein the Compound of Formula I is:

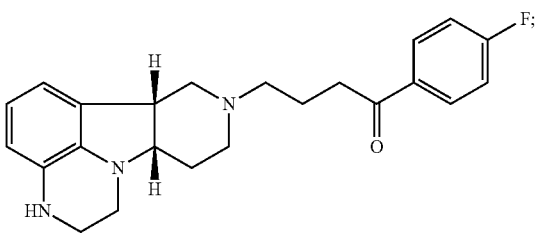 [SMILES: O=C(CCCN1CC[C@H]2[C@@H](C1)c1cccc3c1N2CCN3)c1ccc(F)cc1]

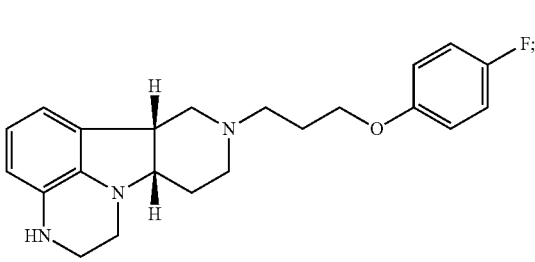 [SMILES: Fc1ccc(OCCCN2CC[C@H]3[C@@H](C2)c2cccc4c2N3CCN4)cc1]

2.13 any of the preceding methods wherein the Compounds of Formula I (i) bind to 5-HT2A, e.g., with a $K_i$ of less than 25 nM, preferably less than 10 nM, more preferably 1 nM; and (ii) does not bind to $D_2$ receptors and/or SERT or bind to dopamine $D_2$ receptors and/or SERT, e.g., with a $K_i$ of greater than 50 nM, preferably greater than 75 nM, more preferably greater than 100 nM, in a binding assay as described in the Example 1 below;

2.14 any of the preceding methods wherein the Compounds of Formula I (i) bind to 5-HT2A, e.g., with a $K_i$ of less than 5 nM, preferably less than 1 nM, and does not bind or only bind to dopamine $D_2$ receptors, SERT, α1A, 5-HT2C or H1 receptors, e.g., with a $K_i$ of greater than 50 nM, preferably greater than 75 nM, more preferably greater than 100 nM, in a binding assay as described in example 1 below;

2.15 Any of the foregoing methods, wherein the effective amount to treat one or more sleep disorders is an amount sufficient to bind to 5-HT2A receptors, e.g., with a $K_i$ of less than 25 nM, preferably less than 10 nM, more preferably 1 nM, but does not bind to $D_2$ receptors and/or SERT or bind to $D_2$ receptors and/or SERT, e.g., with a $K_i$ of greater than 50 nM, preferably greater than 75 nM, more preferably greater than 100 nM in an assay as described in Example 1 below;

2.16 Any of the foregoing methods, wherein the sleep disorder include sleep maintenance insomnia, frequent awakenings, and waking up feeling unrefreshed;

2.17 Any of the foregoing methods, wherein the sleep disorder is sleep maintenance insomnia;

2.18 Any of the foregoing methods, wherein the effective amount is 1 mg-5 mg, preferably 2.5-5 mg;

2.19 Any of the foregoing methods, wherein the effective amount is 2.5 or 5 mg.

2.20 Any of the foregoing methods wherein the sleep disorder is in a patient suffering from or at risk of dyskinesia, e.g., a patient receiving dopaminergic medications, e.g., selected from levodopa and levodopa adjuncts (carbidopa, COMT inhibitors, MAO-B inhibitors), dopamine agonists, and anticholinergics, e.g., receiving levodopa.

2.21 Any of the foregoing methods wherein the patient suffers from Parkinson's disease.

Compounds of the Invention may exist in free or salt form, e.g., as acid addition salts. In this specification unless otherwise indicated language such as Compounds of the Invention is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included. Pharmaceutically acceptable salts include, for example, the hydrochloride and tosylate salts. Where dosage amounts of salts are given by weight, e.g., milligrams per day or milligrams per unit dose, the dosage amount of the salt is given as the weight of the corresponding free base, unless otherwise indicated.

The invention also provides the foregoing methods, e.g., Method I, e.g., any of 1.1-1.39, or Method II, e.g., any of 2.1-2.19, wherein the Compound of Formula I, in free or pharmaceutically acceptable salt form is administered in a composition, wherein said Compound of Formula I in free or pharmaceutically acceptable salt form in admixture with a pharmaceutically acceptable diluent or carrier.

The invention further provides a Pharmaceutical Composition (Composition I) comprising a Compound of Formula I in free or pharmaceutically acceptable salt form, e.g., as described in any of Methods I or 1.1-1.37, in admixture with a pharmaceutically acceptable diluent or carrier for use in any of Methods I or 1.1-1.37.

The invention further provides a Pharmaceutical Composition (Composition II) comprising a Compound of Formula I in free or pharmaceutically acceptable salt form, e.g., as described in any of Method II, e.g., any of 2.1-2.19, in admixture with a pharmaceutically acceptable diluent or carrier for use in any of Method II, e.g., any of 2.1-2.19.

In another aspect, the invention provides use of a Compound of Formula I or a pharmaceutical composition comprising a Compound of formula I in free or pharmaceutically acceptable salt form as described in Methods I or 1.1-1.37, in the manufacture of a medicament for the treatment of one or more disorders involving serotonin 5-HT2A, dopamine $D_2$ and/or serotonin reuptake transporter (SERT) pathway as described in any of Methods I or 1.1-1.37.

In another aspect, the invention provides use of a Compound of Formula I or a pharmaceutical composition comprising a Compound of formula I in free or pharmaceutically acceptable salt form as described in Methods II or 2.1-2.19, in the manufacture of a medicament for the treatment of one or more sleep disorders as described in any of Methods II or 2.1-2.19.

In another aspect, methods which involve use of a Compound of Formula I or a pharmaceutical composition comprising a Compound of Formula I in free or pharmaceutically acceptable salt form as described in Methods I-A or II-A, for the treatment of sleep disorders, depression, psychosis, or any combinations thereof, in patients suffering from the listed diseases and/or Parkinson's disease, as described in any of Methods I-A or II-A, or 3.1-3.34.

DETAILED DESCRIPTION OF THE INVENTION

Methods of Making Compounds of the Invention

The compounds of the formula I and their pharmaceutically acceptable salts may be made using the methods as described and exemplified in any of the following patents or applications: U.S. Pat. Nos. 6,548,493; 7,238,690; 6,552,017; 6,713,471; U.S. RE39680; U.S. RE39679; PCT/US08/03340; U.S. application Ser. No. 10/786,935; and U.S. Provisional Application No. 61/036,069. If not commercially available, starting materials for these processes may be made by procedures, which are selected from the chemical art using techniques which are similar or analogous to the synthesis of known compounds. All references cited herein are hereby incorporated in their entirety by reference.

The words "treatment" and "treating" are to be understood accordingly as embracing prophylaxis and treatment or amelioration of symptoms of disease as well as treatment of the cause of the disease.

The term "patient" may include a human or non-human patient.

Compounds of the Invention refer to Compounds of Formula I, which include:

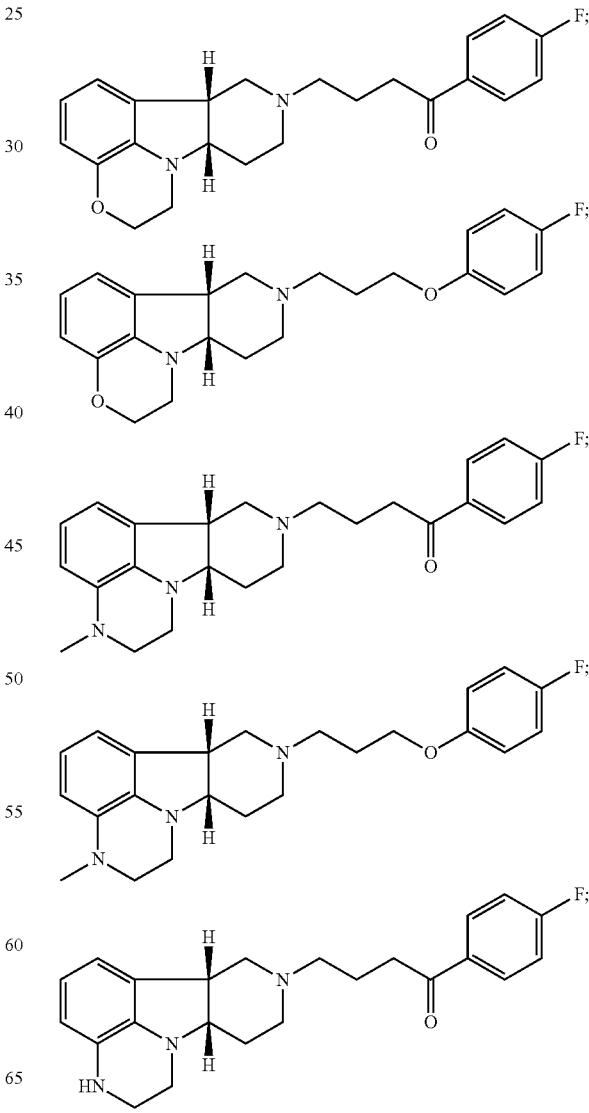

-continued

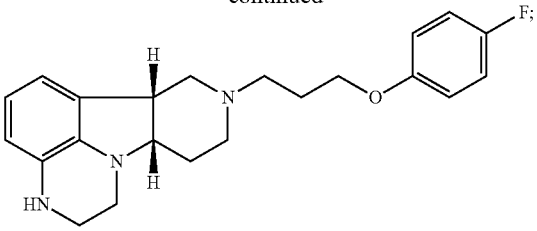

in free or pharmaceutically acceptable salt form. Compounds of the invention are useful in any of Method I, or 1.1-1.37, particularly useful for the treatment of (1) sleep disorder, e.g., sleep maintenance insomnia; (2) depression in patients suffering from psychosis or Parkinson's disease; (3) psychosis, e.g., schizophrenia, in a patient suffering from depression; or (4) mood disorder associated with psychosis, e.g., schizophrenia, or Parkinson's disease. Compounds of the invention are also useful for any of Method II or 2.1-2.19, particularly for the treatment of sleep disorder, e.g., sleep maintenance insomnia.

The phrase "depression in a patient suffering from psychosis" may include depressed patients suffering from a co-morbid psychotic disorder such as schizophrenia or it may include psychotic depressed patients wherein such patients suffer from severe depression wherein such depression accompanies hallucinations and/or delusions.

The term "sleep maintenance insomnia" refers to the inability to stay asleep or to resume sleep after waking in the middle of the sleep cycle.

The terms "Compounds of Formula I" and "Compounds of the Invention" may be used interchangeably and may be used as a sole therapeutic agent, or they may also be used in combination or for co-administration with other active agents.

The discovery of the selective receptor profiles of the Compounds of Formula I not only provides effective treatment of 5-HT2A, SERT and/or $D_2$ receptor related disorders without or with minimal extrapyramidal side effects as claimed in the current invention, but also provides insight for the design of a combination therapy for the treatment of related disorders, wherein a Compound of Formula I may be used in combination with second therapeutic agents, particularly at lower dosages than when the individual agents are used as a monotherapy so as to enhance the therapeutic activities of the combined agents without causing the undesirable side effects commonly occur in conventional monotherapy. For example, as Compounds of the Invention bind to 5-HT2A, $D_2$ and/or SERT and are useful for treating patients with a combination of disorders, e.g., (a) psychosis with a co-morbid disorder of depression and/or sleep disorder; (b) depression with a co-morbid disorder of psychosis; (c) sleep disorder in patients suffering from psychosis, Parkinson disease, and/or depression; or (d) any combinations thereof, Compounds of Formula I may be simultaneously, sequentially, or contemporaneously administered with other anti-depressant, anti-psychotic, other hypnotic agents, and/or agents use to treat Parkinson's disease or mood disorders. In another example, side effects may be reduced or minimized by administering a Compound of Formula I in combination with one or more second therapeutic agents in free or salt form, wherein the dosages of the second therapeutic agent(s) or both Compound of Formula I and the second therapeutic agents are lower than if the agents/compounds are administered as a monotherapy.

In a particular embodiment, the Compounds of Formula I are useful to treat dyskinesia in a patient receiving dopaminergic medications, e.g., selected from levodopa and levodopa adjuncts (carbidopa, COMT inhibitors, MAO-B inhibitors), dopamine agonists, and anticholinergics, e.g., such as are used in the treatment of Parkinson's disease.

As demonstrated above, Compounds of Formula I have a wide separation between 5-$HT_{2A}$ and $D_2$ receptor affinities than other atypical antipsychotic drugs (~60 fold). They reduce L-DOPA-induced dyskinetic behavior. Without intending to be bound by theory, it is hypothesized that this is accomplished by virtue of the potent 5-$HT_{2A}$ antagonism with minimal interference with L-DOPA-induced motor correction, by virtue of the low relative $D_2$ receptor activity. Parkinson's disease results from loss of DA neurons in the substantia nigra pars compacta. The primary motor symptoms of PD are treated by L-DOPA. Activation of medium spiny neurons in the dorsolateral striatum that project to the substantia nigra pars reticulata results in disinhibition of thalamocortical neurons and increased motor activity. Overactivity of this "direct" striatal pathway may contribute to the expression of dyskinesias. 5-$HT_{2A}$ receptors are localized in striatal medium spiny neurons. Compounds of Formula I are thus believed to block dyskinesias by blockade of 5-$HT_{2A}$ receptors.

In another aspect of the current invention, Method I, e.g., any of 1.1-1.37, or Method II, e.g., any of 2.1-2.19, further comprises one or more therapeutic agents selected from compounds that modulate GABA activity (e.g., enhances the activity and facilitates GABA transmission), a GABA-B agonist, a 5-HT modulator (e.g., a 5-HT1a agonist, a 5-HT2a antagonist, a 5-HT2a inverse agonist, etc.), a melatonin agonist, an ion channel modulator (e.g., blocker), a serotonin-2 antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, a neurokinin-1 drug, an anti-depressant, and an antipsychotic agent, e.g., an atypical antipsychotic agent, in free or pharmaceutically acceptable salt form (Method I-A and II-A respectively).

In a further embodiment of this aspect, the invention provides Method I-A or II-A as follows, further comprising one or more therapeutic agents.

3.1 Method I-A or II-A, wherein the therapeutic agent(s) is compounds that modulate GABA activity (e.g., enhances the activity and facilitates GABA transmission);

3.2 Method I-A or II-A or 3.1, wherein the GABA compound is selected from a group consisting of one or more of doxepin, alprazolam, bromazepam, clobazam, clonazepam, clorazepate, diazepam, flunitrazepam, flurazepam, lorazepam, midazolam, nitrazepam, oxazepam, temazapam, triazolam, indiplon, zopiclone, eszopiclone, zaleplon, Zolpidem, gabaxadol, vigabatrin, tiagabine, EVT 201 (Evotec Pharmaceuticals) and estazolam;

3.3 Method I-A or II-A, wherein the therapeutic agent is an additional 5HT2a antagonist;

3.4 Method I-A or II-A or 3.3, wherein said additional 5HT2a antagonist is selected from one or more of ketanserin, risperidone, eplivanserin, volinanserin (Sanofi-Aventis, France), pruvanserin, MDL 100907 (Sanofi-Aventis, France), HY10275 (Eli Lilly), APD125 (Arena Pharmaceuticals, San Diego, Calif.), and AVE8488 (Sanofi-Aventis, France);

3.5 Method I-A or II-A, wherein the therapeutic agent is a melatonin agonist;
3.6 Method I-A or II-A or 3.5, wherein the melatonin agonist is selected from a group consisting of one or more of melatonin, ramelteon (ROZEREM®, Takeda Pharmaceuticals, Japan), VEC-162 (Vanda Pharmaceuticals, Rockville, Md.), PD-6735 (Phase II Discovery) and agomelatine;
3.7 Method I-A or II-A, wherein the therapeutic agent is an ion channel blocker;
3.8 Method I-A or II-A or 3.7, wherein said ion channel blocker is one or more of lamotrigine, gabapentin and pregabalin.
3.9 Method I-A or II-A, wherein the therapeutic agent is an orexin receptor antagonist;
3.10 Method I-A or II-A or 3.9, wherein the orexin receptor antagonist is selected from a group consisting of orexin, a 1,3-biarylurea, SB-334867-a (GlaxoSmithKline, UK), GW649868 (GlaxoSmithKline) and a benzamide derivative;
3.11 Method I-A or II-A, wherein the therapeutic agent is the serotonin-2 antagonist/reuptake inhibitor (SARI);
3.12 Method I-A or II-A or 3.11, wherein the serotonin-2 antagonist/reuptake inhibitor (SARI) is selected from a group consisting of one or more Org 50081 (Organon—Netherlands), ritanserin, nefazodone, serzone and trazodone;
3.13 Method I-A or II-A, wherein the therapeutic agent is the 5HT1a agonist;
3.14 Method I-A or II-A or 3.13, wherein the 5HT1a agonist is selected from a group consisting of one or more of repinotan, sarizotan, eptapirone, buspirone and MN-305 (MediciNova, San Diego, Calif.);
3.15 Method I-A or II-A, wherein the therapeutic agent is the neurokinin-1 drug;
3.16 Method I-A or II-A or 3.15, wherein the neurokinin-1 drug is Casopitant (GlaxoSmithKline);
3.17 Method I-A or II-A, wherein the therapeutic agent is an antipsychotic agent;
3.18 Method I-A or II-A or 3.17, wherein the antipsychotic agent is selected from a group consisting of chlorpromazine, haloperidol, droperidol, fluphenazine, loxapine, mesoridazine molidone, perphenazine, pimozide, prochlorperazine promazine, thioridazine, thiothixene, trifluoperazine, clozapine, aripiparazole, olanzapine, quetiapine, risperidone, ziprasidone and paliperidone;
3.19 Method I-A or II-A, wherein the therapeutic agent is an anti-depressant;
3.20 Method I-A or II-A or 3.19, wherein the anti-depressant is selected from amitriptyline, amoxapine, bupropion, citalopram, clomipramine, desipramine, doxepin, duloxetine, escitaloprame, fluoxetine, fluvoxamine, imipramine, isocarboxazid, maprotiline, mirtazapine, nefazodone, nortriptyline, paroxetine, phenlzine sulfate, protiptyline, sertraline, tranylcypromine, trazodone, trimipramine, and velafaxine;
3.21 Method I-A or II-A, 3.17 or 3.18, wherein the antipsychotic agent is an atypical antipsychotic agent;
3.22 Method I-A or II-A, or any of 3.17-3.21, wherein the atypical antipsychotic agent is selected from a group consisting of clozapine, aripiparazole, olanzapine, quetiapine, risperidone, ziprasidone, and paliperidone;
3.23 Method I-A or II-A, wherein the therapeutic agent is selected from any of methods 3.1-3.22, e.g., selected from a group consisting of modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazapam, triazolam, indiplon, zopiclone, eszopiclone, zaleplon, Zolpidem, gabaxadol, vigabatrin, tiagabine, EVT 201 (Evotec Pharmaceuticals), estazolam, ketanserin, risperidone, eplivanserin, volinanserin (Sanofi-Aventis, France), pruvanserin, MDL 100907 (Sanofi-Aventis, France), HY10275 (Eli Lilly), APD125 (Arena Pharmaceuticals, San Diego, Calif.), AVE8488 (Sanofi-Aventis, France), repinotan, sarizotan, eptapirone, buspirone, MN-305 (MediciNova, San Diego, Calif.), melatonin, ramelteon (ROZEREM®, Takeda Pharmaceuticals, Japan), VEC-162 (Vanda Pharmaceuticals, Rockville, Md.), PD-6735 (Phase II Discovery), agomelatine, lamotrigine, gabapentin, pregabalin, orexin, a 1,3-biarylurea, SB-334867-a (GlaxoSmithKline, UK), GW649868 (GlaxoSmithKline), a benzamide derivative, Org 50081 (Organon—Netherlands), ritanserin, nefazodone, serzone, trazodone, Casopitant (GlaxoSmithKline), amitriptyline, amoxapine, bupropion, citalopram, clomipramine, desipramine, doxepin, duloxetine, escitaloprame, fluoxetine, fluvoxamine, imipramine, isocarboxazid, maprotiline, mirtazapine, nefazodone, nortriptyline, paroxetine, phenlzine sulfate, protiptyline, sertraline, tranylcypromine, trazodone, trimipramine, velafaxine, chlorpromazine, haloperidol, droperidol, fluphenazine, loxapine, mesoridazine molidone, perphenazine, pimozide, prochlorperazine promazine, thioridazine, thiothixene, trifluoperazine, clozapine, aripiparazole, olanzapine, quetiapine, risperidone, ziprasidone and paliperidone;
3.24 Method I-A or II-A, wherein the therapeutic agent is an H3 agonist;
3.25 Method I-A or II A, wherein the therapeutic agent is an H3 antagonist;
3.26 Method I-A or II-A, wherein the therapeutic agent is a noradrenergic antagonist;
3.27 Method I-A or II-A, wherein the therapeutic agent is a galanin agonist;
3.28 Method I-A or II-A, wherein the therapeutic agent is a CRH antagonist;
3.29 Method I-A or II-A, wherein the therapeutic agent is a human growth hormone;
3.30 Method I-A or II-A, wherein the therapeutic agent is a growth hormone agonist;
3.31 Method I-A or II-A, wherein the therapeutic agent is estrogen;
3.32 Method I-A or II-A, wherein the therapeutic agent is an estrogen agonist;
3.33 Method I-A or II-A, wherein the therapeutic agent is a neurokinin-1 drug;
3.34 Method I-A or II-A, wherein a therapeutic agent is combined with compounds of Formula (I) and the therapeutic agent is an anti-Parkinson agent such as L-dopa, co-careldopa, duodopa, stalova, symmetrel, benzotropine, biperiden, bromocryiptine, entacapone, pergolide, pramipexole, procyclidine, ropinirole, selegiline and tolcapone.
3.35 Method I-A or II-A, wherein compounds of Formula (I) may be used to treat sleep disorders, depression, psychosis, or any combinations thereof, in patients suffering from the listed diseases and/or Parkinson's disease.
3.36 Method I-A or II-A, wherein the disorder is selected from at least one or more of psychosis, e.g., schizophrenia, depression, mood disorders, sleep disorders (e.g., sleep maintenance and/or sleep onset) or any combination of disorders thereof;

3.37 Any of the foregoing methods wherein the disorder is sleep disorder;

3.38 Any of the foregoing methods, wherein the disorder is sleep disorder associated with psychosis, e.g., schizophrenia or Parkinson's disease;

in free or pharmaceutically acceptable salt form.

In another aspect of the invention, the combination of a Compound of Formula I and one or more second therapeutic agents as described in Methods I-A, II-A or any of 3.1-3.23, may be administered as a composition. The combination compositions can include mixtures of the combined drugs, as well as two or more separate compositions of the drugs, which individual compositions can be, for example, co-administered together to a patient.

The person of skill in the art, in possession at the receptor binding profile of the Compounds of Formula I together with those of other drugs, can design combination therapies having optimal receptor activity to enhance efficacy and reduce side effects.

In a particular embodiment, Method I-A and Method II-A comprises administering to a patient in need thereof, a Compound of Formula I in combination with an atypical antipsychotic agent, e.g., a compound selected from clozapine, aripiparazole, olanzapine, quetiapine, risperidone, ziprasidone, or paliperidone, in free or pharmaceutically acceptable salt form, for example wherein the dosage of the atypical antipsychotic agent is reduced and/or side effects are reduced.

In another embodiment, Method I-A and Method II-A comprises administering to a patient in need thereof, a Compound of Formula I in combination with an anti-depressant, e.g., amitriptyline, amoxapine, bupropion, citalopram, clomipramine, desipramine, doxepin, duloxetine, escitaloprame, fluoxetine, fluvoxamine, imipramine, isocarboxazid, maprotiline, mirtazapine, nefazodone, nortriptyline, paroxetine, phenlzine sulfate, protiptyline, sertraline, tranylcypromine, trazodone, trimipramine, or velafaxine, in free or pharmaceutically acceptable salt form.

Alternatively, the anti-depressant may be used as an adjunct medication in addition to the compound of Formula I.

In still another embodiment, Method I-A or II-A comprises administering to a patient in need thereof, a Compound of Formula I in combination with a compound that modulates GABA activity, e.g., a compound selected from doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gabaxadol, vigabatrin, tiagabine, EVT 201 (Evotec Pharmaceuticals), estazolam or any combinations thereof, in free or pharmaceutically acceptable salt form. In another preferred embodiment, Method I-A or II-A comprises administering to a patient in need thereof, a Compound of Formula I in combination with doxepin in free or pharmaceutically acceptable salt form. Dosages of doxepin can vary in any range known to a person of ordinary skill in the art. In one example, a 10 mg dose of doxepin may be combined with any dosage of a compound of Formula I.

In another embodiment, Method I-A or II-A comprises administering to a patient in need thereof, a Compound of Formula I in combination (including as part of a daily dosage regimen) with an atypical stimulant, e.g., a modafinil, adrafinil, or armodafinil. A regimin incorporating a Compound of Formula I with such drugs promotes more regular sleep, and avoids side effects such as psychosis or mania associated with higher levels of such drugs, e.g., in the treatment of bipolar depression, cognition associated with schizophrenia, and excessive sleepiness and fatigue in conditions such as Parkinson's disease and cancer.

The dosages of a Compound of Formula I and/or the second therapeutic agents of Method I-A and II-A can be the same as or lower than the approved dosage for the drug, the clinical or literature test dosage or the dosage used for the drug as a monotherapy. In a preferred embodiment, the dosages of a Compound of Formula I and/or the second therapeutic agents of Method I-A and II-A are lower than when used in a monotherapy. Therefore, in a particular embodiment, the dosage of a Compound of Formula I is lower than 100 mg once daily, preferably less than 50 mg, more preferably less than 40 mg, still more preferably less than 30 mg, still more preferably less than 20 mg, still more preferably less than 10 mg, still more preferably less than 5 mg, most preferably less than 2.5 mg. In particular embodiments, the second therapeutic agent of Method I-A and II-A is doxepin and the dosage of doxepin is between about 0.001 mg and 49 mg. Preferably, the amount of doxepin is between about 0.0001 mg and 20 mg, between about 0.001 mg and 10 mg, more preferably between about 0.01 mg and 9 mg, and still more preferably between about 0.01 mg and 6 mg.

In another preferred embodiment, the dosages of both the Compound of Formula I and the second therapeutic agent of Method I-A and II-A are lower than the dosages used for the individual drug as a monotherapy. Therefore, in a particular embodiment, for example, Method I-A or II-A comprises administering (1) a Compound of Formula I at a dosage lower than 100 mg once daily, preferably less than 50 mg, more preferably less than 40 mg, still more preferably less than 30 mg, still more preferably less than 20 mg, still more preferably less than 10 mg, still more preferably less than 5 mg, most preferably less than 2.5 mg; and (2) doxepin at a dosage of less than 50 mg, more preferably, less than 20 mg, still more preferably, less than 10 mg, most preferably less than 6 mg, in free or pharmaceutically acceptable salt form.

In an especially embodiment, Method I-A or II-A comprises administering to a patient in need thereof (1) a Compound of Formula I at a dosage of less than 5 mg, more preferably less than 2.5 mg; and (2) doxepin at a dosage of less than 10 mg, preferably less than 6 mg, in free or pharmaceutically acceptable salt form.

In some preferred embodiments, Method I-A or II-A is a method for the treatment of sleep disorders associated with psychosis, e.g., sleep disorders associated with schizophrenia or Parkinson's disease. In another preferred embodiment, Method I-A or II-A is a method for the treatment of psychosis, e.g., schizophrenia or Parkinson's disease in patients suffering from insomnia. In still another preferred embodiments, Method I-A or II-A is a method for the treatment of one or more sleep disorders.

The term "conventional antipsychotic agents" or "conventional antipsychotic drugs" or "antipsychotic agents" include, but are not limited to droperidol, fluphenazine, loxapine, mesoridazine molidone, perphenazine, pimozide, prochlorperazine promazine, thioridazine, thiothixene, trifluoperazine, clozapine, aripiparazole, olanzapine, quetiapine, risperidone and ziprasidone. Other conventional antipsychotic agents also include chlorpromazine, haloperidol and paliperidone. Conventional antipsychotic agents are divided into typical and atypical antipsychotic agents. Typical antipsychotic agents include but are not limited to chlorpromazine, droperidol, fluphenazine, haloperidol, loxapine, mesoridazine molidone, perphenazine, pimozide, prochlorperazine promazine, thioridazine, thiothixene and trifluoperazine. Atypical antipsychotic agents include but are not limited to clozapine, aripiparazole, olanzapine, quetiapine, risperidone, ziprasidone, and paliperidone. Therefore, patients who are unable to tolerate the side effects of conventional antipsychotic agents refer to patients who are unable to tolerate the side effects of the agents as described above. Consequently, such patients would benefit from a monotherapy of a Compound of Formula I (e.g., Method I), wherein Compound of Formula I targets 5HT2A receptors without or with minimal interaction with $D_2$ receptors. In addition, these patients would also benefit from a combination therapy comprising a Compound of Formula I and one or more second therapeutic agents (e.g., Method I-A or II-A) wherein the dosages of the second agent(s) or both the second agents and the Compound of Formula I are lower than when they are administered as a monotherapy. As such, undesirable side effects may be reduced or minimized.

The term "GABA" refers to gamma-aminobutyric acid. The GABA compounds of Method I-A or II-A are compounds which bind to the GABA receptor, and include, but are not limited to one or more of doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gabaxadol, vigabatrin, tiagabine, EVT 201 (Evotec Pharmaceuticals) or estazolam.

Additional 5HT2a antagonist of Method I-A or II-A include, but are not limited to, one or more of ketanserin, risperidone, eplivanserin, volinanserin (Sanofi-Aventis, France), pruvanserin, MDL 100907 (Sanofi-Aventis, France), HY10275 (Eli Lilly), APD125 (Arena Pharmaceuticals, San Diego, Calif.), or AVE8488 (Sanofi-Aventis, France).

The 5HT1a agonist may be, for example, one or more of repinotan, sarizotan, eptapirone, buspirone or MN-305 (MediciNova, San Diego, Calif.).

The melatonin agonist of Method I-A or II-A include, but are not limited to, one or more of melatonin, ramelteon (ROZEREM®, Takeda Pharmaceuticals, Japan), VEC-162 (Vanda Pharmaceuticals, Rockville, Md.), PD-6735 (Phase II Discovery) or agomelatine.

The ion channel blocker of Method I-A or II-A include, but are not limited to, one or more of lamotrigine, gabapentin or pregabalin.

The orexin receptor antagonist of Method I-A or II-A include, but are not limited to, one or more of orexin, a 1,3-biarylurea, SB-334867-a (GlaxoSmithKline, UK), GW649868 (GlaxoSmithKline) or a benzamide derivative, for example.

The serotonin-2 antagonist/reuptake inhibitor (SARI) of Method I-A or II-A include, but are not limited to, one or more of Org 50081 (Organon—Netherlands), ritanserin, nefazodone, serzone or trazodone.

The neurokinin-1 drug of Method I-A or II-A includes, but are not limited to, Casopitant (GlaxoSmithKline).

The term "antidepressant" or "other antidepressant" may include amitriptyline, amoxapine, bupropion, citalopram, clomipramine, desipramine, doxepin, duloxetine, escitaloprame, fluoxetine, fluvoxamine, imipramine, isocarboxazid, maprotiline, mirtazapine, nefazodone, nortriptyline, paroxetine, phenlzine sulfate, protiptyline, sertraline, tranylcypromine, trazodone, trimipramine, velafaxine, in free or pharmaceutically acceptable salt forms.

Dosages employed in practicing the present invention will of course vary depending, e.g. on the particular disease or condition to be treated, the particular Compound of the Invention used, the mode of administration, and the therapy desired. Unless otherwise indicated, an amount of the Compound of the Invention for administration (whether administered as a free base or as a salt form) refers to or is based on the amount of the Compound of the Invention in free base form (i.e., the calculation of the amount is based on the free base amount). Compounds of the Invention may be administered by any suitable route, including orally, parenterally or transdermally, but are preferably administered orally. In general, satisfactory results for Method I or any of 1.1-1.37, e.g. for the treatment of a combination of diseases such as a combination of at least depression, psychosis, e.g., (1) psychosis, e.g., schizophrenia, in a patient suffering from depression; (2) depression in a patient suffering from psychosis, e.g., schizophrenia; (3) mood disorders associated with psychosis, e.g., schizophrenia, or Parkinson's disease; and (4) sleep disorders associated with psychosis, e.g., schizophrenia, or Parkinson's disease, as set forth above are indicated to be obtained on oral administration at dosages of the order from about 1 mg to 100 mg once daily, preferably 2.5 mg-50 mg, e.g., 2.5 mg, 5 mg, 10 mg, 20 mg, 30 mg, 40 mg or 50 mg, once daily, preferably via oral administration. Satisfactory results for Method II or any of 2.1-2.19, e.g. for the treatment of sleep disorder alone are indicated to be obtained on oral administration at dosages of the order from about 2.5 mg-5 mg, e.g., 2.5 mg, 3 mg, 4 mg or 5 mg, of a Compound of Formula I, in free or pharmaceutically acceptable salt form, once daily, preferably via oral administration. Satisfactory results for Method I-A are indicated to be obtained at less than 100 mg, preferably less than 50 mg, e.g., less than 40 mg, less than 30 mg, less than 20 mg, less than 10 mg, less than 5 mg, less than 2.5 mg, once daily. Satisfactory results for Method II-A are indicated to be obtained at less than 5 mg, preferably less than 2.5 mg·ss The phrase "pharmaceutically acceptable salts" refers to derivatives of the above disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the Compounds of the Invention can be synthesized from the parent compound which contains a basic or acidic moiety by conventional chemical methods. Generally, such salts can be prepared by reacting the free base forms of these compounds with a stoichiometric amount of the appropriate acid in water or in an organic solvent, or in a mixture of the two; generally, nonaqueous media like ether, ethyl acetate, ethanol, isopropanol, or acetonitrile are preferred. Further details for the preparation of these salts, e.g., toluenesulfonic salt in amorphous or crystal form, may be found in PCT/US08/03340 and/or U.S. Provisional Appl. No. 61/036,069.

Pharmaceutical compositions comprising Compounds of the Invention may be prepared using conventional diluents or excipients and techniques known in the galenic art. Thus oral dosage forms may include tablets, capsules, solutions, suspensions and the like.

EXAMPLES

Example 1: Binding Assay for 5-HT2A, Dopamine $D_2$, SERT, αA1, 5-HT2C and H1 Receptors Binding studies for 5-HT2A, dopamine $D_2$, SERT, αA1, 5-HT2C and H1 receptors are well known in the art and may be used to determine the binding affinities of the Compounds of the Invention. A Compound of Formula I, 1-(4-Fluoro-phenyl)-4-((6bR, 10aS)-3-methyl-2,3,6b,9, 10, 10a-hexahydro-1H, 7H-pyrido[3',4', 4,5]pyrrolo[1,2,3-de] quinoxalin-8-yl)-butan-1-one (Compound A) is selected for detailed evaluation. The compound exhibits binding affinity profiles for 5-HT2A, D2, SERT, αA1, 5-HT2C and H1 as disclosed in Table 1 and Table 2 compared to known antipsychotic agents.

A representative method for performing the binding studies may be found in Fitzgerald et al., J. Neurochem. 1999 May; 72(5): 2127-34, the disclosure of which is incorporated by reference.

1-(4-[125I] iodo-2,5-dimethoxyphenyl)-2-aminopropane ([125] DOI; 2, 200 Ci/mmol), N-[3H]methylspiperone (50 Ci/mmol), [3H]Prazosin (77 Ci/mmol), and lysergic acid diethylamide(N-methyl-[3H]([3H]-LSD; 73 Ci/mmol) were purchased from New England Nuclear (Boston, Mass., U.S.A.) [3H] 8-hydoxy-DPAT (217 Ci/mmol) and [3H] Mesulergine (50 Ci/mmol) were purchased from Pharmacia Amersham (Arlington Heights, Ill., U.S.A.). All other reagents were purchased from Research Biochemical International (Natick, Mass., U.S.A.), Sigma Chemical Co. (St. Louis, Mo., U.S.A.) or GibcoBRL unless otherwise noted.

Membrane receptors: Cell lines stably expressing recombinant human 5-HT2A receptors were generated by calcium phosphate mediated transfection with plasmids containing receptor cDNAs (Fitzgerald et al., 1999)

Stable expression of 5-HT2A and 5-HT2C receptors in human embryonic kidney 293 Epstein-Barr nuclear antigen (HEK293E) cells. Stable cell lines were generated by transfecting HEK293E cells with plasmids containing human 5-HT2A or 5-HT2C (VNV edited isoform cDNA using calcium phosphate. These plasmids also contained the cytomegalovirus intermediate early promoter to drive receptor expression, Epstein-Bar virus oriP for their maintenance as an extrachromosomal element, and the hph gene from *Escherichia coli* to yield hygromycin B resistance (Horlick et al, 1997; Rominger et al., 1998). Transfected cells were maintained in Dulbecco's modified Eagle's medium (DMEM) containing dialyzed 10% fetal bovine serum at 37 degrees Celsius in a humid environment (5% CO2) for 10 days. The 5-HT2A cells were adapted to spinner culture for bulk processing, whereas it was necessary to maintain the 5-HT2C line as adherent cultures. On the day of harvest, cells were washed in phosphate-buffered saline, counted and stored at −80 degrees Celsius.

Membrane preparations On the day of assay, pellets of whole cells (containing $1\times10^8$ cells expressing the receptor of interest were thawed on ice and homogenized in 50 mM Tris-HCL (ph 7.7) containing 1.0 mM EDTA using a Brinkmann Polytron (PT-10; setting of 6 for 10s). The homogenate was centrifuged at 48,000 g for 10 minutes, and the resulting pellet was washed twice by repeated homogenization and centrifugation steps. The final pellet was resuspended in tissue buffer, and protein content was determined by the method of Bradford (1976) using bovine serum albumin as the standard.

Transfected HEK293 cells (adherent) expressing human 5-HT2B and 5-HT1A receptors provided membrane source for these assays. Cell lines expressing rat D2-short and human D4 receptors were generated by calcium phosphate mediated transfection of Chinese hamster ovary (CHO) cells with plasmids containing receptor cDNAs. Membranes prepared from rat frontal cortex and frozen liver were used for alpha-1A and alpha-1B adrenergic receptor binding.

Measurement of Agonist and Antagonist Radioligand Binding to 5-HT2A and 5-HT2C Receptors N-[3H] Methylspiperone and [3H] mesulergine were used as the antagonist radioligands for the 5HT2A and 5HT2C receptors, respectively, whereas [125I]DOI was used as the agonist radioligand for both receptors. The high efficacy partial agonist [125I]DOI was chosen over the full agonist [3H]-5HT because [3H]-5HT gave inadequate levels of specific binding with the lower density 5-HT2C line. In addition, the relatively weak binding affinity of 5-HT for the 5-HT2A receptor precluded its use as a radioligand. Equilibrium binding conditions for each radioligand at each receptor were established and optimized with respect to time, temperature, and protein concentration before saturation and competition experiments were conducted.

For the agonist radioligand binding studies, assays were conducted in disposable polypropylene 96-well plates (Costar Corporation, Cambridge, Mass., U.S.A.) and were initiated by addition of membrane homogenate in tissue buffer (10-30 micrograms per well.) to assay buffer (50 mM Tris-HCL, 0.5 mM EDTA, 10 mM pargyline, 10 mM MgSO4, and 0.05% ascorbic acid, pH 7.5) containing [125] DOI (final concentration, 0.3-0.5 nM with or without competing ligand. The reaction mixture was incubated to equilibrium for 45 min at 37 degrees Celsius and terminated by rapid filtration (cell harvester, Inotech Biosystems, Lansing, Mich., U.S.A.) over GFF glass filter membranes that had been presoaked in 0.3% polyethylenimine. Filters were washed in ice-cold 50 mM Tris-HCL buffer (ph 7.5) and then counted for radioactivity in a gamma counter at 80% efficiency. For saturation studies, 14 concentrations of [125I] DOI up to a maximal concentration of 6 nM were used. Specific binding at each concentration was determined in the presence of 10 micromolar mianserin. For competition experiments, a fixed concentration of [125]DOI (0.3-5 nM) was competed with duplicate concentrations of ligand (12 concentrations ranging from 10 picomolar to 10 micromolar).

For the antagonist radioligands, saturation experiments for [3H] mesulergine and N-[3H]methylspiperone were conducted to establish the equilibrium binding parameters of these radio-ligands for the 5-HT2C and 5-HT2A receptors, respectively. The assay buffer used in the [3H] mesulergine assays was identical to that used in the [125I] DOI assay except for the addition of 10 mM CaCl2 for 10 mM MgSO4. The assay buffer used for the N-[3H]methylspiperone assays was identical to that in the [125I] DOI assay except for the exclusion of 20 mM NaCl. 5-HT2C membrane homogenate (40 micrograms of protein per well) was incubated with 14 concentrations of [3H]mesulergine (up to a final concentration of 20 nM for 45 minutes at 37 degrees Celsius. For the 5-HT2A assay, membrane homogenate (40 micrograms of protein per well) was incubated with 14 concentrations of N-[3H] methylspiperone for 30 minutes at 37 degrees Celsius. Excess (10 micromolar) mianserin or ketanserin was used to define nonspecific binding in the 5-HT2C and the 5-HT2A assays, respectively. Assays were conducted and terminated as described for the agonist radioligand assays except that the filters were counted for radioactivity by liquid scintillation spectroscopy.

Data Analysis

The equilibrium disassociation constants (Kd values) and maximal number of binding sites (Bmax values) from the saturation experiments and apparent dissociation constants (Ki values) from the competition experiments were calculated using an iterative nonlinear regression curve-fitting program (GraphPad Prism, San Diego, Calif., U.S.A.)

Citalopram as a radioligand at a concentration of 0.7 nM. In this assay, the Kd for [3H]—N-Methyl-Citalopram was 2.5 nM with a Bmax of 425 fmol/mg protein. The assay was validated using clomipramine (Ki=0.2 nM), citalopram (Ki=3.0 nM), and imipramine (Ki=4.0 nM).

The third assay was conducted at Cerep (Celle L'Evescault, France). The third assay was a radioligand binding assay in human recombinant serotonin transporter in CHO cells using [3H]-imipramine as the radioligand at a concentration of 2 nM. The assay was validated with unlabeled imipramine. (Ki=2.7 nM).

TABLE 1

| Receptors | Compound A* | Haloperidol | Aripiprazole | Clozapine | Olanzapine | Quetiapine | Risperidone | Ziprasidone |
|---|---|---|---|---|---|---|---|---|
|   |   |   |   | $K_i$ (nM) |   |   |   |   |
| 5-HT2A | 0.54 | 100 | 9 | 9.6 | 2.5 | 202 | 0.5 | 0.28 |
| D$_2$ | 31.9 | 0.7 | 1.6 | 190 | 31 | 400 | 5.9 | 5 |
| SERT | 33-72 | >1,000 | 240-405 | >1,000 | >10,000 | >1,000 | ~1,000 | 112 (cloned) >1,000 (platelet) |
| α1A | 73 | 11 | 26 | 19 | 60 | 20 | 2.3 | 6 |
| 5-HT2C | 173 | 3949 | 130 | 13 | 7.1 | 2000 | 63 | 10 |
| H1 | >100 | 780 | 28 | 1 | 2 | 10 | 14 | 15 |

TABLE 2

SERT Activities of selected Compounds of the Invention compared to other Antipsychotic agents

|   | Human platelet membrane binding using $^3$H—N-methyl-Citalopram | Rat forebrain synaptosomal membrane binding with $^3$H—N-methyl-Citalopram | Recombinant human SERT in CHO cell membranes binding $^3$H-IMI |
|---|---|---|---|
|   | $K_i$ (nM) |   |   |
| Compound A | 72 | 46 | 33 |
| Aripiprazole | 405 | 207 | 240 |
| Risperidone | 10,000 | 10,000 |   |
| Olanzapine | 10,000 | >10,000 |   |
| Reference | IMI | IMI | IMI |
| Reference Value | 10.6 | 44 | 2.7 |
| Reference Value Repeated | 7.1 | 41 |   |

Example 2: Effectiveness of the Compounds of Formula I as Antidepressant in Chronic Animal Model of Depression Experimental Procedure for Table II:

Two different assays used to characterize affinity for the serotonin transporter were conducted at Caliper Life Sciences (Hopkinton, Mass.), a company that acquired NovaScreen. One assay (#100-0056), Transporter SERT, was a radioligand binding assay in rat forebrain using [3H]—N-Methyl-Citalopram as the radioligand at a concentration of 0.7 nM. [3H]—N-Methyl-Citalopram has a Kd (binding affinity) of 1.7 n and a Bmax of 33.1 fmol/mg protein, The assay was validated using the following reference agent, imipramine (IMI) (Ki=40.9 nM). Other reference agents which may be used include paroxetine (Ki=0.1 nM); fluoxetine (Ki=1.4 nM); clomipramine (Ki=2.8 nM), serotonin (Ki=55.6 nM), and zimeldine (Ki=68.3 nM).

The other assay, Transporter SERT (h) was a radioligand binding assay in human platelets using [3H]—N-Methyl-

EXPERIMENTAL DESIGN

Anti-depressant activity of a Compound of Formula I (Compound A) is measured using the social defeat (resident-intruder) mouse model for depression in which induced social withdrawal in rodents has been shown to be responsive to chronic, but not acute, anti-depressant drug treatment. The social defeat paradigm is based on the observation that psychosocial stress produces long-lasting alterations in the motivation of mice for social contact. Mice are subjected to a 10 day training period in which they are exposed to daily bouts of social stress, i.e., exposure to a different aggressive mouse ('aggressor') each day. They are then observed for their social behavior by measuring their tendency to approach an unfamiliar mouse, i.e., to spend time in the "Interaction Zone" which is in close proximity to the unfamiliar intruder. Mice are recorded by videotape and scored for social behavior (i.e., time in the Interaction Zone) and aversive behavior (i.e., time in the Corner Zones). Whereas normal mice display social interactions with unfamiliar mice (i.e., spend more time in the Interaction Zone), those mice exposed to repeated social defeat conditions display aversive reactions (i.e., spend more time in the Corner Zones) and spend less time than normal mice in contact with the unfamiliar test mouse (i.e., resident intruder or TARGET).

The aversive responses of 'socially defeated' mice are resilient; aversive behavior persists for weeks and can be elicited even 4 weeks after the end of the 10 day social stress exposure. The aberrant behavior of 'socially defeated' mice is responsive to chronic anti-depressant medications. Mice treated daily for 30 days with the anti-depressant drugs, fluoxetine or imipramine, display improved social interaction behavior (i.e., spend more time in the Interaction Zone versus the Corner Zones) when once again exposed to an unfamiliar mouse. Notably, chronic, but not acute, fluoxetine treatment improves social behavior. Since social behaviors measured by the social defeat paradigm, like human depression, are differentially responsive to chronic anti-depressant therapy, this paradigm may more accurately reflect beneficial actions of novel anti-depressant therapies, providing an advantage over traditional models (such as, Forced Swim and Tail Suspension models) that respond to acute pharmacological effects of drugs that are not necessarily predictive of chronic antidepressant efficacy.

A representative compound of the present invention, Compound A, is tested in the social defeat paradigm. Normal male mice or mice subjected to social defeat stress once daily for 10d (N=8-12 C57Bl/6 mice/group) are injected once daily for 29d Compound A (1 mg/kg, IP) or vehicle solution (5% DMSO/5% Tween-20/15% PEG400/75% water). On day 30, all mice are tested for their social response to an unfamiliar mouse. Normal mice treated with Compound A once daily for 30 d are healthy and normal-appearing and gained weight normally. These mice spend comparable time in the Interaction Zone as mice receiving the vehicle injection. As anticipated, mice that are subjected to 10 d of social stress showed profound social defeat behavior, spending less than half the amount of time in the vicinity of an unfamiliar mouse than normal un-stressed mice. Socially-defeated mice treated chronically with Compound A, however, exhibited a significant increase in social behavior, spending almost twice as much time in the Interaction Zone when exposed to an unfamiliar mouse compared with socially-defeated mice receiving vehicle injections. Thus, the amount of time spent in the Interaction Zone by socially-defeated mice receiving Compound A is indistinguishable from normal mice receiving vehicle injections. Thus, socially-defeated mice spend significantly more time in the distant Control Zone(s) compared with normal (non-stressed) mice. The administration of a compound of the present invention significantly reverses this behavioral preference.

Taken together, these data demonstrate that daily administration of Compound A induce a behavioral response in socially-stressed mice consistent with antidepressant efficacy and comparable to that elicited by anti-depressant medications such as fluoxetine.

Example 3: Effectiveness in Alleviating L-Dopa Induced Dyskinesia

Reduction in axial, orolingual and limb abnormal involuntary movements using standard Abnormal Involuntary Movement Scale (AIMS) in dyskinesic mice injected daily with the compound in combination with L-DOPA indicates that co-administration of Compounds of Formula I reduces development and expression of AIMS associated with dyskinetic behavior (orolingual, axial, and limb) and locomotor activity (locomotive AIMS). Unilateral 6-OHDA-lesioned mice are administered a Compound of Formula I (Compound A) in accordance with the following schedule:
Control:
Day 1-Day 9: Treatment with L-DOPA/benserazide
Day 10: Treatment with L-DOPA/benserazide+Evaluation of AIMs (dyskinesia)

Experiment 1 (Chronic): Development of Dyskinesia

Day 1-Day 10: Treatment with L-DOPA/benserazide plus ITI-007 ITI-007PD.
Day 11: Treatment with L-DOPA/benserazide+Evaluation of AIMs (dyskinesia)

Experiment 2 (Acute): Expression of Dyskinesia

Day 1-Day 10: Treatment with L-DOPA/benserazide
Day 11: Treatment with L-DOPA/benserazide plus ITI-007+Evaluation of AIMs (dyskinesia)
Compound A (0.3 mg/kg IP) reduces dyskinetic behaviors after chronic co-administration with levodopa (10 mg/kg IP) to unilateral 6-OHDA-lesioned mice. The compound effectively reduces (by ~50%) the development of dyskinetic behaviors in PD mice (i.e., Chronic treatment group). It has a less robust but still significant effect (by ~25% reduction) on established dyskinetic behaviors (i.e., Acute treatment group). Taken together, these data suggest that Compounds of Formula I have utility for the prevention and treatment of L-DOPA-induced dyskinesias in PD. In addition to reducing L-DOPA-Induced Dyskinesias, as described above, the Compounds of Formula I will also reduce PD psychosis and depression, improve poor night time sleep and reduce excessive daytime sleepiness.

Example 4—Clinical Trial for Low Dose for Sleep Maintenance Insomnia and Sleep Disorders Associated with Psychiatric and Neurological Diseases As described above, at low doses, Compounds of Formula I are primarily serotonin 5-HT2A antagonists. At higher doses, the compounds also act as a pre-synaptic partial agonist, post-synaptic antagonist at D2 dopamine receptors and inhibits the serotonin transporter. The present study evaluates a range of doses of a Compound of Formula (Compound A) in patients with sleep maintenance insomnia (SMI). The main objectives of this study are to determine if the compound decreases wake time after sleep onset (WASO) as a measure of sleep maintenance efficacy and if the compound increases slow wave sleep (SWS) as a biomarker for 5-HT2A brain receptor occupancy.

The study is a randomized, double-blind, complete crossover design. Eighteen patients experiencing SMI, aged 18 to 65, are included in the efficacy analysis. All subjects receive three single doses of Compound A and placebo, administered in the evening before overnight PSG recordings with one week washout between doses. SWS, WASO, other PSG measures, and safety are analyzed.

Compound A dose-dependently decreases WASO (p=0.032) and increases SWS (p=0.002). Compound A preserves normal sleep architecture over the course of the night. Compound A is safe and well tolerated. Compound A dose-dependently and robustly decreases WASO in patients with SMI, suggesting efficacy for improved sleep maintenance. The magnitude of effect on WASO at the highest tested dose suggests that the unique pharmacological profile of Compounds of Formula I is useful in maintaining sleep above and beyond that provided by 5-HT2A antagonism. In addition, increases in SWS sleep suggest that significant occupancy of brain 5-HT2A receptors is occurring. Compounds of Formula I are useful for patients with SMI and for the treatment of sleep disorders associated with psychiatric and neurological diseases.

| Improved Sleep as Measured by PSG (Sleep Efficiency defined as time asleep/time in bed) | | | | |
|---|---|---|---|---|
| Outcome Measure | Mean Change from Baseline (min) | | | Dose-Response Trend Analysis |
| (n = 18) | Placebo | 1 mg | 5 mg | 10 mg | p-value |
| SWS | −3.75 | 0.47 | 5.53 | 8.94 | p = 0.002 |
| WASO | −1.86 | −12.69 | −14.31 | −33.22 | p = 0.001 |

Improved Sleep as Measured by PSG (Sleep Efficiency defined as time asleep/time in bed)

| Outcome Measure | Mean Change from Baseline (min) | | | | Dose-Response Trend Analysis |
|---|---|---|---|---|---|
| (n = 18) | Placebo | 1 mg | 5 mg | 10 mg | p-value |
| Total Sleep Time | −9.22 | 4.17 | 0.56 | 27.61 | p < 0.001 |
| Total Time Awake | 9 | −4.08 | −1.42 | −28.31 | p < 0.001 |
| Sleep Efficiency | −1.94 | 0.82 | 0.14 | 5.80 | p < 0.001 |

The compound causes no change on latency to REM (p=0.143) and no change in duration of REM (p=0.124). The compound does not impair latency to fall asleep (p=0.455). The compound increases slow wave sleep during the first half of the night (first quarter p=0.022; second quarter p=0.029) and increases stage 2 sleep during the second half of the night (third quarter p=0.048, fourth quarter p=0.004). The compound is safe and well-tolerated in patients with sleep maintenance insomnia. There are no serious adverse events. There are no dose-related adverse events or changes in safety parameters. The compound does not impair cognitive function as measured in the morning after PSG by the Digit Symbol Substitution Test (DSST), the Word Pair Associates Test (WPAT), or the Leeds Psychomotor Test.

Striatal D2 receptor occupancy in healthy volunteers using positron emission tomography is dose dependent. The doses evaluated for sleep disorder are shown to be below doses where there is high striatal D2 occupancy.

| Dose | 10 mg | 20 mg | 30 mg |
|---|---|---|---|
| % Striatal D2 Occupancy | ~12% | ~20% | ~32% |

The invention claimed is:

1. A method for the treatment of bipolar depression, comprising administering to a patient in need thereof a Compound of Formula I:

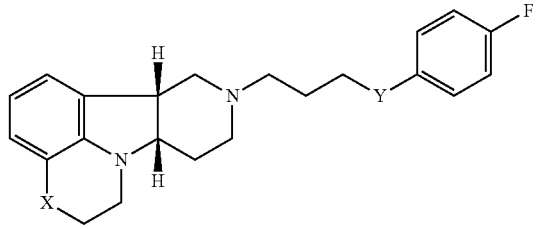

Formula I wherein X is O, —NH or —N(CH$_3$); and Y is —O— or —C(O)—, in free or pharmaceutically acceptable salt form.

2. The method of claim 1, wherein the Compound of Formula I is

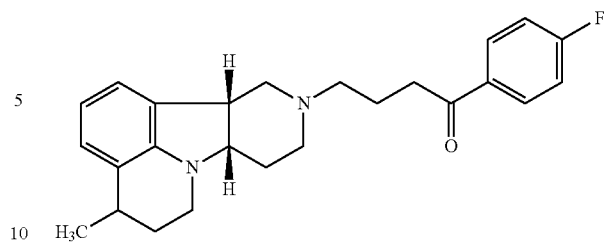

in free or pharmaceutically acceptable salt form.

3. The method according to claim 1 wherein said patient is unable to tolerate the side effects of conventional antipsychotic drugs.

4. The method according to claim 3 wherein said antipsychotic drugs are selected from the group consisting of haloperidol, aripiprazole, clozapine, olanzapine, quetiapine, risperidone and zipasidone.

5. The method according to claim 1, wherein said patient is suffering from psychosis or Parkinson's disease.

6. The method according to claim 1, wherein patient is suffering from depression.

7. The method according to claim 1, wherein said patient is suffering from psychosis.

8. The method according to claim 1, further comprising administration of one or more therapeutic agents selected from the group consisting of compounds that modulate GABA activity, a GABAB agonist, a 5-HT modulator, a melatonin agonist, an ion channel modulator, a serotonin-2 antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, a neurokinin-1 drug, an anti-depressant, an antipsychotic agent, and an atypical antipsychotic agent, in free or pharmaceutically acceptable salt form.

9. The method according to claim 1, further comprising administering one or more therapeutic agents selected from the group consisting of modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gaboxadol, vigabatrin, tiagabine, EVT 201, estazolam, ketanserin, risperidone, eplivanserin, volinanserin, pruvanserin, MDL 100907, HY10275, APD125, AVE8488, repinotan, sarizotan, eptapirone, buspirone, MN-305, melatonin, ramelteon, VEC-162, PD-6735, agomelatine, lamotrigine, gabapentin, pregabalin, orexin, a 1,3-biarylurea, SB-334867-a, GW649868, a benzamide derivative, Org 50081, ritanserin, nefazodone, serzone, trazodone, Casopitant, amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelzine sulfate, protriptyline, sertraline, tranylcypromine, trazodone, trimipramine, venlafaxine, chlorpromazine, haloperidol, droperidol, fluphenazine, loxapine, mesoridazine molindone, perphenazine, pimozide, prochlorperazine promazine, thioridazine, thiothixene, trifluoperazine, clozapine, aripiparazole, olanzapine, quetiapine, risperidone, ziprasidone and paliperidone, in free or pharmaceutically acceptable salt form.

10. The method according to claim 1, wherein the amount of said Compound of Formula I administered is from 0.1 mg to 20 mg, in free or pharmaceutically acceptable salt form, provided that in the case of a salt, the weight is calculated as the free base.

11. The method according to claim 10, wherein the amount of the Compound of Formula I administered is 0.5-10 mg.

12. The method according to claim 10, wherein the amount of the Compound of Formula I administered is 2.5-5 mg.

13. The method according to claim 10, wherein the amount of the Compound of Formula I administered is less than 5 mg.

14. The method according to claim 10, wherein the amount of the Compound of Formula I administered is less than 2.5 mg.

15. The method of claim 2 wherein the Compound of Formula I is in the form of the tosylate salt.

16. The method according to claim 1, further comprising administering one or more therapeutic agents selected from a group consisting of L-dopa, co-careldopa, duodopa, symmetrel, benzotropine, biperiden, bromocriptine, entacapone, pergolide, pramipexole, procyclidine, ropinirole, selegiline and tolcapone.

17. The method according to claim 10, further comprising administering one or more therapeutic agents selected from a group consisting of L-dopa, co-careldopa, duodopa, stalova, symmetrel, benzotropine, biperiden, bromocriptine, entacapone, pergolide, pramipexole, procyclidine, ropinirole, selegiline and tolcapone.

18. A method for promoting regular sleep in the treatment:
of bipolar depression;
comprising administering to a patient in need thereof:
an atypical stimulant; and
a Compound of Formula I:

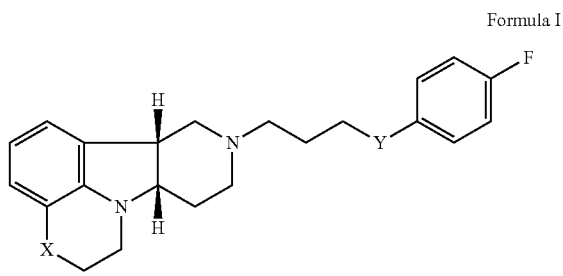

Formula I wherein X is O, —NH or —N(CH$_3$); and Y is —O— or —C(O)—, in free or pharmaceutically acceptable salt form.

19. The method according to claim 18, wherein the compound of Formula I has the structure:

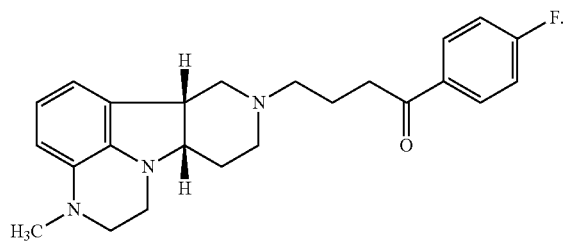 [SMILES: CN1CCN2c3c(cccc31)[C@@H]1CN(CCCC(=O)c3ccc(F)cc3)CC[C@@H]12]

20. The method according to claim 19 wherein the Compound of Formula I is in the form of the tosylate salt.

21. The method according to claim 20, wherein the amount of said Compound of Formula I administered is from 0.1 mg to 20 mg, in free or pharmaceutically acceptable salt form, provided that in the case of a salt, the weight is calculated as the free base.

22. The method according to claim 21, wherein the amount of the Compound of Formula I administered is 0.5-10 mg.

23. The method according to claim 22, wherein the amount of the Compound of Formula I administered is 2.5-5 mg.

24. The method according to claim 22, wherein the amount of the Compound of Formula I administered is less than 5 mg.

25. The method according to claim 22, wherein the amount of the Compound of Formula I administered is less than 2.5 mg.

26. The method according to claim 18, wherein the atypical stimulant is selected from the group consisting of modafinil, adrafinil and armodafinil.

27. The method according to claim 18, further comprising administration of one or more therapeutic agents selected from the group consisting of compounds that modulate GABA activity, a GABAB agonist, a 5-HT modulator, a melatonin agonist, an ion channel modulator, a serotonin-2 antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, a neurokinin-I drug, an anti-depressant, and an antipsychotic agent, in free or pharmaceutically acceptable salt form.

28. The method according to claim 18, further comprising administration of one or more therapeutic agents selected from the group consisting of modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gaboxadol, vigabatrin, tiagabine, EVT 201, estazolam, ketanserin, risperidone, eplivanserin, volinanserin, pruvanserin, MDL 100907, HY10275, APD125, AVE8488, repinotan, sarizotan, eptapirone, buspirone, MN-305, melatonin, ramelteon, VEC-162, PD-6735, agomelatine, lamotrigine, gabapentin, pregabalin, orexin, a 1,3-biarylurea, SB-334867-a, GW649868, a benzamide derivative, Org 50081, ritanserin, nefazodone, serzone, trazodone, Casopitant, amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelzine sulfate, protriptyline, sertraline, tranylcypromine, trazodone, trimipramine, venlafaxine, chlorpromazine, haloperidol, droperidol, fluphenazine, loxapine, mesoridazine molindone, perphenazine, pimozide, prochlorperazine promazine, thioridazine, thiothixene, trifluoperazine, clozapine, aripiparazole, olanzapine, quetiapine, risperidone, ziprasidone and paliperidone, in free or pharmaceutically acceptable salt form.

* * * * *